(12) United States Patent
Rajala et al.

(10) Patent No.: US 7,666,160 B2
(45) Date of Patent: Feb. 23, 2010

(54) DELIVERY DEVICE

(75) Inventors: Gregory J. Rajala, Neenah, WI (US); Daniel James Heuer, Fremont, WI (US); Steven Craig Gehling, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 56 days.

(21) Appl. No.: 11/648,217

(22) Filed: Dec. 29, 2006

(65) Prior Publication Data

US 2008/0161752 A1 Jul. 3, 2008

(51) Int. Cl.
*A61F 13/20* (2006.01)
*A61M 31/00* (2006.01)
*A61M 37/00* (2006.01)
*D04H 1/22* (2006.01)
*A61F 6/06* (2006.01)
*A61F 13/02* (2006.01)

(52) U.S. Cl. .............................. 604/13; 604/12; 604/14; 604/15; 604/16; 604/18; 604/93.01; 604/904; 28/118; 28/119; 28/120; 424/430; 424/431

(58) Field of Classification Search .............. 604/14, 604/15, 16, 18, 904, 12, 93.01; 28/118, 119, 28/120; 424/430, 431
See application file for complete search history.

(56) References Cited

U.S. PATENT DOCUMENTS

| | | |
|---|---|---|
| 7,788 A | 11/1850 | Robinson |
| 102,985 A | 5/1870 | Snyder |
| 212,177 A | 2/1879 | Berger |
| 213,588 A | 3/1879 | Palmer |
| 445,579 A | 2/1891 | Weldon |
| 545,102 A | 8/1895 | Sleem |
| 650,080 A | 5/1900 | Marmaduke |

(Continued)

FOREIGN PATENT DOCUMENTS

GB 0 886 034 A 1/1962

(Continued)

OTHER PUBLICATIONS http://en.wikipedia.org/wiki/Vitamin_e online encyclopedia entry for vitamin E. Accessed Nov. 22, 2007.*

*Primary Examiner*—Leslie R Deak
*Assistant Examiner*—Adam Marcetich
(74) *Attorney, Agent, or Firm*—Ralph H. Dean, Jr.; Sebastian C. Pugliese, III; Bryan R. Rosiejka

(57) ABSTRACT

An applicator for introducing a therapeutic substance into a body cavity of a subject in need of the therapeutic substance is provided. The applicator has the look and feel of a conventional tampon applicator but delivers a therapeutic substance. Generally, the applicator has a first outer member having a shape suitable for insertion into a body cavity of a mammal and has a dispensing end and a second end distal to the dispensing end. A second inner member is coaxially and slidably housed within the first member such that one end of the second inner member is within the first member. The applicator of the present invention also has at least one aperture located in a side wall of the outer member. The aperture is located on the side wall of the outer member between the dispensing end and the second end of the outer member.

29 Claims, 11 Drawing Sheets

U.S. PATENT DOCUMENTS

| | | | |
|---|---|---|---|
| 652,848 A | 7/1900 | Hill | |
| 659,130 A | 10/1900 | Bucklin | |
| 695,356 A | 3/1902 | Washburn | |
| 716,040 A | 12/1902 | Holt | |
| 763,081 A | 6/1904 | Tope | |
| 806,188 A | 12/1905 | Rees | |
| 837,085 A | 11/1906 | Loar | |
| 872,217 A | 11/1907 | Bonesteel | |
| 926,960 A | 7/1909 | Pearl | |
| 1,019,465 A | 3/1912 | Harrison et al. | |
| 1,173,031 A | 2/1916 | Pruitt | |
| 1,566,061 A | 12/1925 | Ziegler | |
| 1,584,464 A | 5/1926 | Maranville | |
| 1,616,389 A | 2/1927 | Piercy | |
| 1,670,605 A | 5/1928 | Aeilts | |
| 1,732,337 A | 10/1929 | Miller | |
| 1,763,079 A | 6/1930 | Zacsek | |
| 1,794,221 A | 2/1931 | Washburn et al. | |
| 1,833,598 A | 11/1931 | Smith | |
| 1,903,681 A | 4/1933 | Merliss | |
| 1,923,409 A | 8/1933 | Ziegler | |
| 1,978,677 A | 10/1934 | Kirk | |
| D098,874 S | 3/1936 | Lewis | |
| 2,034,926 A | 3/1936 | Smith | |
| 2,105,946 A | 1/1938 | Lewis | |
| 2,106,707 A | 2/1938 | Greth | |
| 2,112,160 A | 3/1938 | Johnson | |
| 2,112,581 A | 3/1938 | Tacey | |
| 2,120,367 A | 6/1938 | Lewis | |
| 2,130,305 A * | 9/1938 | Lewis | 604/59 |
| 2,509,241 A | 5/1950 | Mende | |
| 2,516,846 A | 8/1950 | Betz | |
| 2,518,486 A | 8/1950 | Mende | |
| 2,590,138 A | 3/1952 | Willis | |
| 2,616,421 A | 11/1952 | Greenberg | |
| 2,616,422 A | 11/1952 | Jones | |
| 2,623,519 A | 12/1952 | Cohen | |
| 2,646,044 A | 7/1953 | Diack | |
| 2,724,385 A | 11/1955 | Lockhart | |
| 2,764,975 A | 10/1956 | Greenberg | |
| 2,841,146 A | 7/1958 | Heuboski | |
| 2,856,926 A | 10/1958 | Senger | |
| 2,856,927 A | 10/1958 | Senger | |
| 2,862,496 A | 12/1958 | Hassler et al. | |
| 2,881,760 A | 4/1959 | McGiveran et al. | |
| 2,925,100 A | 2/1960 | Senger | |
| 2,925,815 A | 2/1960 | Lynn | |
| 3,048,175 A | 8/1962 | Uddenberg | |
| 3,086,527 A | 4/1963 | Forrest | |
| D197,751 S | 3/1964 | Rigney et al. | |
| 3,262,450 A | 7/1966 | Elias | |
| 3,275,000 A | 9/1966 | Bowen | |
| 3,424,158 A | 1/1969 | Silver | |
| 3,506,008 A | 4/1970 | Huck | |
| 3,682,176 A | 8/1972 | Kelsen | |
| 3,749,093 A | 7/1973 | Bloom | |
| 3,817,248 A | 6/1974 | Buckles et al. | |
| 3,831,605 A | 8/1974 | Fournier | |
| 3,847,150 A | 11/1974 | Scheuermann | |
| 3,882,866 A | 5/1975 | Zackheim | |
| 3,886,940 A | 6/1975 | Hunger | |
| 3,985,122 A | 10/1976 | Topham | |
| 3,986,645 A * | 10/1976 | Baldwin et al. | 222/386 |
| 4,048,998 A * | 9/1977 | Nigro | 604/14 |
| 4,071,027 A | 1/1978 | Meador | |
| 4,100,923 A | 7/1978 | Southern | |
| 4,271,835 A * | 6/1981 | Conn et al. | 604/15 |
| 4,301,798 A | 11/1981 | Anderson | |
| 4,341,211 A | 7/1982 | Kline | |
| D266,702 S | 10/1982 | Lagny | |
| 4,365,631 A | 12/1982 | Kline | |
| 4,421,504 A * | 12/1983 | Kline | 604/12 |
| 4,424,054 A * | 1/1984 | Conn et al. | 604/11 |
| 4,469,151 A | 9/1984 | Wilson et al. | |
| 4,496,341 A | 1/1985 | Brucks | |
| D279,504 S | 7/1985 | Tump | |
| 4,636,202 A * | 1/1987 | Lowin et al. | 604/236 |
| 4,678,463 A | 7/1987 | Millar | |
| 4,692,140 A | 9/1987 | Olson | |
| D294,063 S | 2/1988 | Smith | |
| D298,653 S | 11/1988 | Maietta | |
| 4,788,985 A * | 12/1988 | Manning et al. | 600/572 |
| 4,993,432 A | 2/1991 | Shields et al. | |
| D320,084 S | 9/1991 | Stewart et al. | |
| D320,275 S | 9/1991 | Wada et al. | |
| 5,045,058 A * | 9/1991 | Demetrakopoulos | 604/515 |
| 5,213,566 A | 5/1993 | Weissenburger | |
| 5,282,789 A | 2/1994 | Lundy | |
| 5,364,375 A | 11/1994 | Swor | |
| 5,393,528 A | 2/1995 | Staab | |
| 5,397,312 A | 3/1995 | Rademaker et al. | |
| 5,529,782 A | 6/1996 | Staab | |
| 5,531,703 A | 7/1996 | Skwarek et al. | |
| 5,614,230 A | 3/1997 | Weyenberg et al. | |
| 5,683,358 A | 11/1997 | Nielsen et al. | |
| 6,096,047 A | 8/2000 | Smit | |
| 6,123,683 A | 9/2000 | Propp | |
| 6,125,850 A | 10/2000 | Sokal et al. | |
| 6,156,004 A | 12/2000 | Tremaine et al. | |
| 6,168,576 B1 | 1/2001 | Reynolds | |
| 6,224,573 B1 | 5/2001 | Yeager et al. | |
| 6,245,776 B1 | 6/2001 | Skwierczynski et al. | |
| 6,364,854 B1 * | 4/2002 | Ferrer et al. | 604/60 |
| 6,379,341 B1 | 4/2002 | Cho | |
| 6,526,980 B1 | 3/2003 | Tracy et al. | |
| 6,537,260 B1 | 3/2003 | Lamb | |
| 6,554,792 B2 * | 4/2003 | Hughes | 604/85 |
| 6,589,216 B1 | 7/2003 | Abbott et al. | |
| 6,706,728 B2 | 3/2004 | Hedenstrom et al. | |
| D494,676 S | 8/2004 | Dubniczki et al. | |
| D503,798 S | 4/2005 | Monteiro | |
| 2002/0143287 A1 * | 10/2002 | Buzot | 604/14 |
| 2003/0045829 A1 * | 3/2003 | Gehling et al. | 604/11 |
| 2003/0088217 A1 | 5/2003 | Bergeron et al. | |
| 2003/0225358 A1 | 12/2003 | Berman et al. | |
| 2004/0022687 A1 * | 2/2004 | Wuske et al. | 422/99 |
| 2004/0142968 A1 | 7/2004 | Price et al. | |
| 2004/0260252 A1 | 12/2004 | Dipiano et al. | |
| 2006/0213919 A1 * | 9/2006 | Heuer et al. | 221/33 |
| 2006/0247571 A1 * | 11/2006 | Hayes et al. | 604/14 |

FOREIGN PATENT DOCUMENTS

| | | |
|---|---|---|
| GB | 2 010 093 A | 6/1979 |
| WO | WO 2005/035045 A1 | 4/2005 |
| WO | WO 2005/041847 A2 | 5/2005 |

* cited by examiner

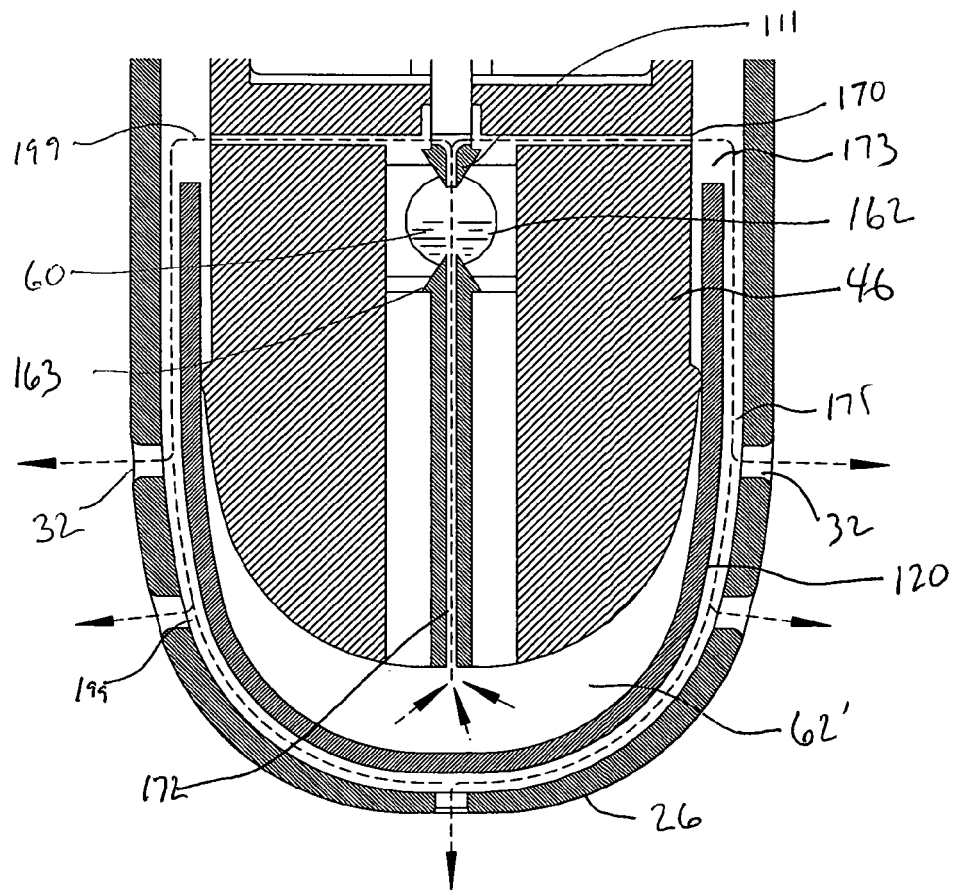
FIG 10
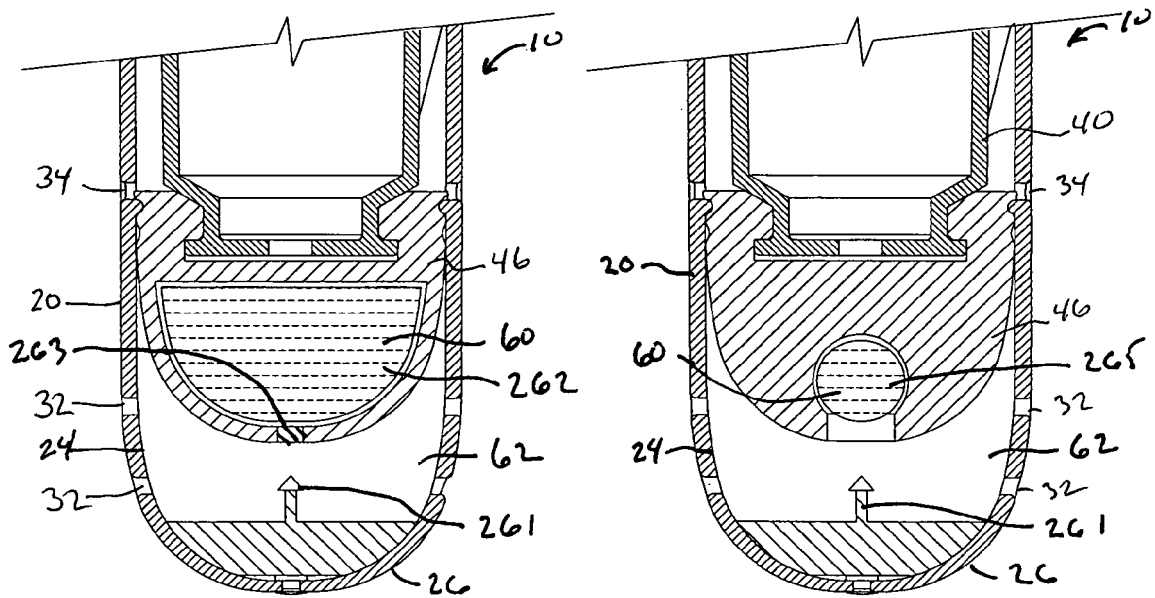
FIG 11
FIG 12

DELIVERY DEVICE

FIELD OF THE INVENTION

The present invention is directed to delivery devices and methods of manufacturing delivery devices used for the application of various therapeutic substances into a body cavity.

BACKGROUND OF THE INVENTION

Symptoms associated with premenstrual syndrome, menstruation, and menopause often occur in women. These symptoms may include dysmenorrheal (menstrual cramping), irritability, water retention, moodiness, depression, anxiety, skin changes, headaches, breast tenderness, tension, weight gain, cravings, fatigue, hot flashes, itching and other associated sensory maladies. Attempts have been made to deliver analgesics in the vicinity of the cervix and the vaginal mucosa using various vaginally-inserted devices and methods to treat or alleviate these symptoms. However, these attempts have drawbacks which make the attempts undesirable for one or more reasons.

One of these attempts has been the use of medicated tampons. Tampons should not be used by women outside of their menstrual period. This severely limits the usefulness of medical products that use a tampon for vaginal delivery of a medication. Even for use in relieving menstrual pain, a tampon delivered medication is only semi-effective since a significant portion of women who suffer with menstrual pain begin experiencing pain prior to menstruation. In addition, a tampon delivered medication could not be used to effectively treat vaginal ailments such as sexually transmitted diseases (STD's) or yeast infections, since medicated tampons should not be used between menstrual periods.

Other methods of applying medication to the vaginal cavity include syringe-like devices. However, past syringes for vaginal delivery of liquid or creme medications have looked like ordinary hypodermic syringes or have looked like aspirator bulbs on the end of tubes and hoses. The devices look intimidating, confusing to use, and appear to be intended for use by a point of care physician or nurse, and not by the person in need of treatment with the therapeutic agent. There is a need in the art for a delivery device to deliver a therapeutic substance to a body cavity, such as the vaginal canal, which is easy to use and is not intimidating to a user.

SUMMARY OF THE INVENTION

Generally stated, in one embodiment of the present invention, provided is an applicator for introducing a therapeutic substance into a body cavity of a subject. The applicator has a first outer member having a shape suitable for insertion into a body cavity of a subject. This first member has at least one side wall, an interior surface, a first dispensing end and a second end distal to the dispensing first end. The dispensing end of the outer member has a dispensing zone having at least one opening. In addition, the side wall joins the first dispensing end of the outer member to the second end of the outer member. The applicator also has a second inner member having a proximate end and a distal end, the second inner member coaxially and slidably housed within the first member such that the proximate end of the second inner member is within the first member, and the distal end of the second inner member extends beyond the second end of the first member. The applicator of the present invention also has at least one aperture located in the side wall of the outer member. The aperture is located at a position on the side wall of the outer member between the dispensing zone and the second end of the outer member.

In a further embodiment of the present invention, the applicator may further be provided with a removable cover. The removable cover serves to cover the at least one opening in the dispensing zone of the first outer member. Exemplary removable covers include a foil, a film, or a cap.

In a further embodiment of the present invention, the applicator has a chamber, which is located at or adjacent to the dispensing end of the first outer member. This chamber is defined by a volume created by the interior surface of the first outer member located at or near the dispensing end of the first outer member and the proximate end of the second inner member. The chamber is adapted to hold a therapeutic substance to be introduced into the body cavity by the applicator.

In an additional embodiment of the present invention, the proximate end of the second inner member of the applicator forms a plunger tip, wherein a portion of the plunger tip directly or indirectly contacts the interior surface of the first outer member. The plunger tip forms an essentially fluid tight seal which essentially prevents any therapeutic substance from escaping the chamber other than through the openings in the dispensing zone.

In another embodiment of the present invention, the interior surface of the first outer member has a detent feature and the second inner member has a complementary structure which allows the detent feature to engage and effectively hold the second inner member in place prior to use. Generally, the detent feature is a protrusion on the interior surface of the first outer member and the second inner member comprises a complementary groove which engages the protrusion. The detent feature serves to help prevent premature ejection of the therapeutic substance from the applicator.

The applicator of the present invention may be used to administer therapeutic substances which are in the form of a liquid, a gas or a solid to a subject in need of treatment with the therapeutic substance. The applicator has the look and feel of a conventional tampon applicator but delivers a therapeutic substance rather than a tampon to the body cavity of the subject being treated with the applicator.

The present invention also provides a method for manufacturing the applicator. In this method, the first outer member is first provided. The therapeutic substance is inserted into the first outer member such that the therapeutic substance contacts the interior surface of the first outer member between the aperture in the side wall of the first outer member and the first dispensing end of the first outer member. The second inner member is then provided and inserted into the first outer member such that the second inner member comes into contact with the therapeutic agent. As the second inner member is inserted any air or other gas trapped between the proximate end of the second inner member and the therapeutic substance is allowed to escape through the aperture in the side wall of the first outer member.

BRIEF DESCRIPTION OF THE DRAWINGS

FIG. 10 shows an enlarged view of the dispensing zone of the applicator of FIG. 9A during dispensing of the therapeutic substance.

FIG. 11 shows another alternative embodiment of the present invention where the therapeutic substance to be administered is located in the plunger tip of the second inner member.

FIG. 12 shows yet another alternative embodiment of the present invention where the substance to be administered is located in a bag structure inserted in the plunger tip of the second inner member.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the terms "therapeutic substance" or "therapeutic agent" are intended to mean substances or compositions which promote a benefit to the subject being treated. Therapeutic substance or agents include medicaments, cleansing products, deodorants, lubricants and other similar substances.

As used herein, the term "subject" is intended to be a living creature in which the therapeutic agent is to be administered. Living creatures include, for example, mammals, reptiles and other creatures.

DETAILED DESCRIPTION OF THE INVENTION

In the following detailed description of the present invention, reference is made to the accompanying drawings which form a part hereof, and in which is shows by way of illustration, specific embodiments in which the invention may be practiced. These embodiments are described in sufficient detail to enable those skilled in the art to practice the invention, and it is to be understood that other embodiments may be utilized and that mechanical, procedural, and other changes may be made without departing from the spirit and scope of the present invention. The following detailed description is, therefore, not to be taken in a limiting sense, and the scope of the present invention is defined only by the appended claims, along with the full scope of equivalents to which such claims are entitled.

The embodiments as described herein will be described in terms of a vaginal applicator as an example of a feminine care product. The embodiments, however, apply equally to other forms of products, such as anally-inserted devices and nasally inserted devices, and should not be limited to the example described herein.

Figure 1:
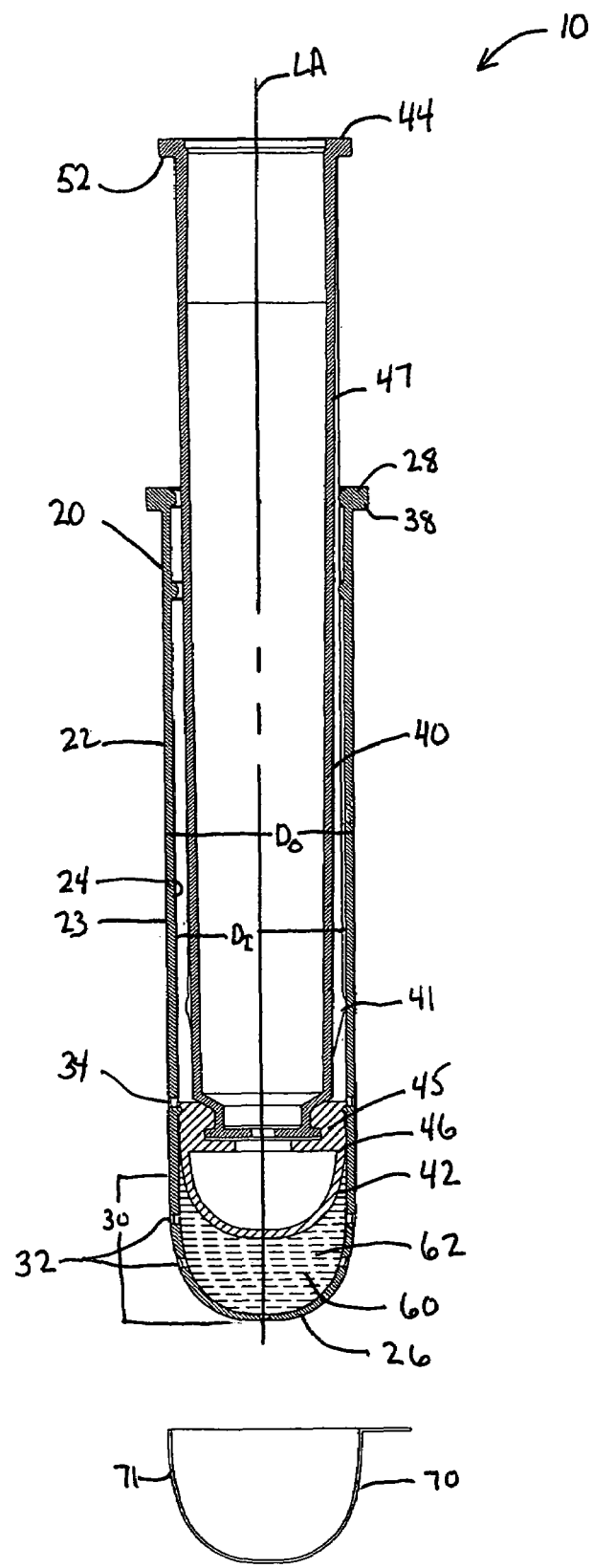
FIG. 1 shows an embodiment of an applicator within the scope of the present invention.

To gain a better understanding of the present invention, attention is directed to FIG. 1. In FIG. 1, an embodiment of an applicator 10 for introducing a substance into a body cavity of a mammal is shown. The applicator 10 has a first outer member 20 having a shape suitable for insertion into a body cavity of a mammal. The applicator 10 also has a second inner member 40, which is coaxially and slidably housed within the first outer member 20.

As shown in FIG. 1, the first outer member 20, also referred to herein as the "first member", has at least one side wall 22, an exterior surface 23, an interior surface 24, a first dispensing end 26, also referred to herein as the "dispensing end", and a second end 28 distal to the first dispensing end 26. In addition, the first member 20 has a longitudinal axis LA, and a caliper or diameter $D_o$ measured perpendicular to the longitudinal axis LA. The dispensing end 26 of the first member 20 has a dispensing zone 30, wherein the dispensing zone has at least one opening 32. The dispensing zone 30 is the portion of the first member 20 which will allow a substance to be administered to the subject being treated with the applicator by being transported from the interior surface side 24 of the first member 20 to the exterior surface 23 of the first member 20. The opening 32 may be an aperture which goes through the first member 20, and the opening 32 provides a way for a substance to be transported from the interior surface 24 of the first member 20 to the exterior surface 23 of the first member 20. There may be a single opening 32 in the dispensing zone 30, or there may be a plurality of openings 32 in the dispensing zone, as is shown in FIG. 1. In addition, the openings 32 may be in the form of a hole, a slit or other similar structures which penetrate the first member 20 from the exterior surface 23 to the interior surface 24.

The side wall 22 joins the first dispensing end 26 of the first member 20 to the second end 28 of the first member 20. The second end 28 of the first member is distal to the dispensing end 26, meaning the second end 28 is at an opposite end of the first member 20 from the dispensing end 26.

The first member 20 is generally a hollow tube having a generally, cylindrical shape. Other shapes may be used for the first member, but from the standpoint of ease of insertion and ease of production, it is desired that the first member 20 have a generally cylindrical shape. By "generally cylindrical" it is meant that the cross-section of the first member is circular in nature. By "circular in nature" it is meant that the cross section may be circular or have a curvilinear shape, such as an elliptical shape. It is possible that the first member 20 is tapered such that the caliper or diameter of the first member 20 gradually increases from the dispensing end 26 to the second end 28. If a tapered first member is used, it is desirable that the outer caliper or diameter $D_o$ of the first member 20 not vary by more than 2 mm over the length L of the first member 20, since the ease of use of the applicator 10 may be reduced. Typically, however, the first member 20 is not tapered.

Generally, the outer caliper or diameter $D_o$ of the first member 20 should generally be in the range of about 8 mm to about 20 mm, for human vaginal or anal applications. It is noted, however, that the outer caliper or diameter $D_o$ may be smaller or larger depending on the particular intended use. For example, in the case of larger animals, the size of the applicator could be increased. In a similar manner, in the case of a nasal applicator or for smaller animals, the size of the applicator could be reduced. The first member 20 may also be commonly referred to in the art as an "outer tube", "inserter tube" or "housing tube". These terms are interchangeable with one another.

The first outer member 20 may be prepared from a wide variety of materials, including those materials which have been conventionally used in the art for tampon applicators. Examples of such materials may be paper, paperboard, cardboard, thermoplastic resins, or a combination of such materials. When the first outer member is prepared from paper, paperboard, or cardboard, the outer tube may be spirally wound, convolutedly wound or a longitudinally seamed hollow tube. However, from the standpoint of user comfort, it is desirable that the first outer member 20 of the applicator 10 is prepared from a thermoplastic resin. Suitable thermoplastic materials include, for example, polyolefins, such as low density polyethylene and low density polypropylene, polyesters, polyurethanes, ethylene vinyl acetate and polystyrene or the like. Other materials may be used, including biodegradables polymer such as polylactic acid or polyvinyl alcohol.

The first outer member 20 may be further configured to have a substantially smooth exterior surface 23, which will facilitate insertion of the first member 20 of the applicator into a woman's vagina or other body cavity, such as an anus or a nostril. When the exterior surface 23 is smooth and/or slippery, the first member 20 will easily slide into a woman's vagina or other body cavity without subjecting the internal tissues of the vagina or other body cavity to abrasion. The first member 20 may be coated to give the exterior surface 23 of the first member a high slip characteristic. Wax, polyethylene, a combination of wax and polyethylene, cellophane, and clay are representative coatings that may be applied to the first member 20 to facilitate comfortable insertion. The first member 20 itself may be formulated to give it a high slip characteristic, including the addition of additives to the resin which may be used to form the first member 20, or by an alteration in physical structure of the exterior surface 23, such as adding pebbling or other bumps to decrease the amount of surface area in contact with the vagina or other epithelium.

The applicator 10 has at least one aperture 34 located in the side wall 22 of the first outer member 20. The aperture 34 is located at a position on the side wall 22 of the first outer member 20 between the dispensing zone 30 and the second end 28 of the first outer member 20. The aperture 34 provides vent or passage for air or gas to escape from the applicator 10 during manufacture of the applicator. If air or gas is present in the applicator 10 during the manufacture and is not released, the pressure inside the first outer member 20 may be increased to a pressure higher than atmospheric pressure, thereby causing the therapeutic agent 60 to leak from the applicator prior to use. Also, an increased pressure or volume of air or gas may be released from the applicator into the body cavity of the user or the subject being treated with the applicator, thereby possibly causing discomfort to the user or the subject being treated. The size of the aperture 34 should be small enough that the aperture does not cause discomfort to the user or subject being treated during insertion into the body cavity, but should be large enough to effectively function as a vent during the manufacture of the applicator filled with the therapeutic agent 60. The aperture 34 may be a hole or a slit in the side wall 22 of the outer member.

As stated above, the applicator also has a second inner member 40 which is coaxially and slidably mounted in the first member 20. The second inner member 40 of the applicator 10 is commonly known as the "plunger" or "inner tube". As with the first member 20, the second inner member 40 may also be generally hollow, however, as will be discussed in more detail below, may have additional features. The second inner member 40 may alternatively be solid or have a unique shape or characteristic outside of the first outer member 20, provided that the unique shape or characteristic does not interfere with the function of the applicator.

The second inner member 40 of the applicator 10 has a first proximate end 42 which is adapted to expel a therapeutic agent 60 from the first outer member 20, through the openings 32 of dispensing zone 30 of the first outer member, when a force is applied to the distal end 44 of the second inner member 40 in a direction towards the first outer member 20. The first proximate end 42 of the second inner member 40 may be housed in the first member 20, such that the proximate end 42 of the second inner member is in contact with the interior surface 24 of the first member 20, as can be seen in FIG. 1. Essentially, some portion of the second inner member 40 should come into contact with the interior surface 24 of the first member 20 by having a portion of the second inner member 40 with it's outer diameter being approximately equal to the inner diameter $D_i$ of the first member 20. This will prevent the second inner member 40 from losing its telescopic relationship with the first member 20. Other ways of ensuring that the second inner member will remain in a telescopic relationship with the first member, known to those skilled in the art, may also be used. For example, as is shown in FIG. 1, the second inner member 40 may have a protrusion or fin 41 which contacts the interior surface 24 of the first member 20. Any other known means known to those skilled in the art may be used to keep the second inner member in a coaxial or telescoping relationship with the first member, so long as the means used does not adversely interfere with the function of the applicator 10 to deliver the therapeutic agent to a user.

In an optional embodiment of the present invention, still referring to FIG. 1, the distal end 44 of the second inner member 40 may optionally be formed such that the distal end forms a finger flange 52 on the distal end 44 of the second inner member 40, which extends outside of the first member. This flange structure 52 provides an enlarged surface onto which the user's forefinger may rest. The finger flange 52 thereby functions as a seat for the forefinger and facilitates movement of the second inner member 40 into the first member 20, during use. In addition, the first member 20 may have a finger grip ring 38 located proximate the second end 28. The finger grip ring 38 provides an enlarged surface onto which one or more fingers of the user may rest. In use, the user may position one or more fingers on the finger grip ring 38 and one or more fingers on the finger flange 52. The user then holds the finger grip ring 38 and pushes the finger flange 52 to move the second inner member 40 toward and further into the first member 20. Other known configurations commonly used on conventional tampon applicators may also be used in the applicator of the present invention.

The second inner member 40 may be prepared from a wide variety of materials, including those materials which have been conventionally used in the art for tampon applicators. Examples of such materials include, for example, paper, paperboard, cardboard, thermoplastic resins, or a combination of such materials. When the first outer member is prepared from paper, paperboard, or cardboard, the outer tube may be spirally wound, convolutedly wound or a longitudinally seamed hollow tube. However, from the standpoint of user comfort, it is desirable that the first outer member 20 of the applicator 10 is prepared from a thermoplastic resin. Suitable thermoplastic materials include, for example, polyolefins, such as low density polyethylene and low density polypropylene, polyesters, polyurethanes, ethylene vinyl acetate and polystyrene or the like. Other materials may be used, including biodegradable polymers such as polylactic acid or polyvinyl alcohol.

The second inner member 40 may be prepared from a single material or may be a combination of materials. In addition, the second inner member may be a one-piece member or may be prepared from two or more pieces. As shown in FIG. 1, the second inner member 40 is prepared from two pieces joined together, wherein the proximate end 42 is prepared from a separate piece of material 45 from the pusher portion 47 of the second inner member 40. This separate piece of material 45 forms a plunger tip 46 on the pusher portion 47 of the second inner member 40. Selection of the material which forms the plunger tip 46 may be based on various factors, including the therapeutic agent to be dispensed from the applicator. In another embodiment of the second inner member 40, the plunger tip 46 can be prepared from a rubber-type material, which will conform to the interior surface 24 of the first outer member, and which will allow the plunger tip 46 of the second inner member 40 to form a fluid tight seal with the interior surface 24 of the first outer member. By having a fluid tight seal, between the plunger tip 46 and the interior surface of the first outer member, the therapeutic agent 60 will remain near the dispensing zone 30 of the first outer member and will be available for dispensing to a user or subject in need of treatment with the therapeutic agent. Suitable materials for use in the plunger tip, which conforms to the interior surface, include rubber materials, such as silicone rubber, nitrile rubber and other similar materials, which will allow the plunger tip 46 to conform to the interior surface 24 of the first outer member. Generally, the plunger tip 46 of the second inner member 40 will have a shape complementary to the shape of the interior surface 24 of the first outer member 20 such that the plunger tip will be able to conform to the interior surface of the first outer member when pushed into a used position.

Alternatively, the plunger tip 46 may be prepared from the same material as the pusher portion 47 of the second inner member 40. In that instance, the plunger tip 46 may be provided with a sealing member 48, which creates a fluid tight seal between the interior surface 24 of the first member and the plunger tip. Again, the fluid tight seal will prevent the therapeutic agent leaking from the applicator 10 prior to use between the plunger tip 46 and the interior surface 24 of the first outer member. In addition, the fluid tight seal helps prevent the therapeutic substance from moving away from the dispensing zone, during storage and during application, making it unavailable for use. Any suitable rubber-like material may be used for the sealing members, including, for example, silicone rubber, nitrile rubber, and other similar material which will deform to the shape of the inside surface 24 of the first outer member 20. Examples of sealing members include, for example, O-rings which will go around the plunger tip 46 of the second inner member. If a sealing member 48 is used, the plunger tip 46 will generally have a seat 49 for the sealing member to be held in place. The seat may be a recess in the plunger tip 46 of the second inner member 40, as is shown in FIG. 2.

Figure 2:
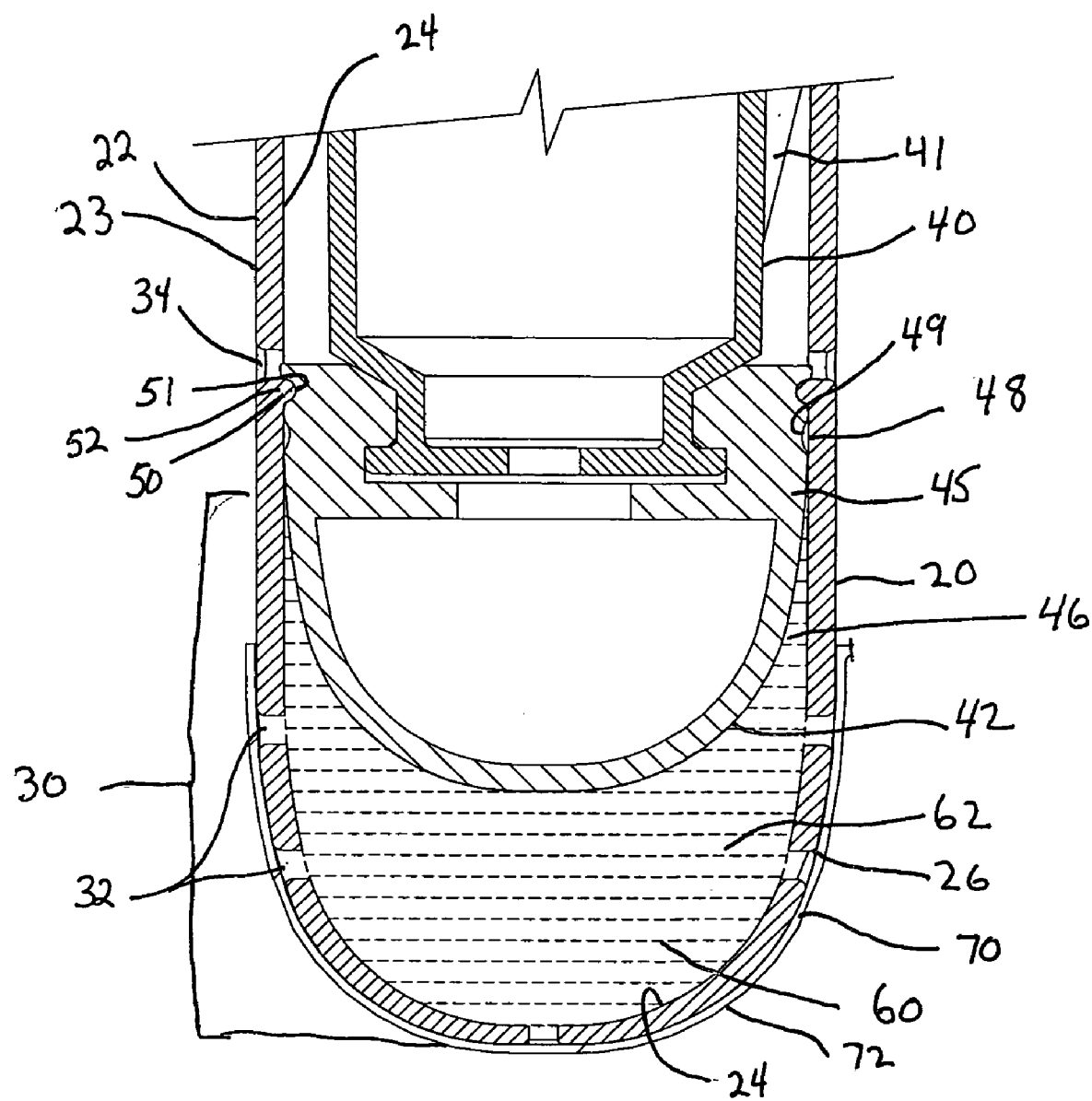
FIG. 2 is an enlarged view of the dispensing zone of an applicator within the scope of the present invention.

As is shown in FIG. 1 and FIG. 2, the interior surface 24 of the first outer member 20 and the proximate end 42 of the second inner member 40 together form a chamber or reservoir 62, which is capable of holding a therapeutic substance or agent 60. The chamber or reservoir 62 is a volume defined by the plunger tip 46 of the second inner member 40 and the interior surface 24 of the first outer member 20 when the second inner member 40 is located in its pre-use position, as is shown in FIGS. 1 and 2.

To assist retaining the therapeutic substance or agent 60 within the chamber or reservoir 62 prior to use, the applicator 10 may optionally have a removable cover 70 applied to the dispensing end 26 and dispensing zone 30 of the first outer member 20. Generally, the removable cover 70 will cover the dispensing zone 30 of the first outer member 20, or at least all of the openings 32 in the dispensing end 26 of the first outer member 20. The removable cover 70 may be a foil, a film, or a cap. A cap 71 is shown in FIG. 1 and a foil or film 72 is shown in FIG. 2. In the case of a film or foil 72, as is shown in FIG. 2, the film or foil 72 may be applied to the first outer member 20 before or after the applicator 10 is filled with the therapeutic substance 60 is formed. The same is true for the cap 71. However, it is generally better to have the removable cover 70 in place prior to filling the applicator 10 with the therapeutic substance 60, since this will help retain the therapeutic substance 60 in the chamber or reservoir 62 during the manufacture of the applicator 10. The removable cover, whether in the form of a foil, film or cap, may also be provided with an opening aid (not shown) which will aid the user in removing the removable cover 70 prior to use. In addition, the cap 71 may provide additional advantages not provided by the foil or film 72. Specifically, the cap 71 may be replaced on the dispensing end 26 on the application 10 after use. This will help prevent any therapeutic substance 60 remaining in the chamber or reservoir 62 after use from leaking out of the chamber or reservoir 62, thereby providing the user with a clean and sanitary way to dispose of the applicator after use.

Figure 3:
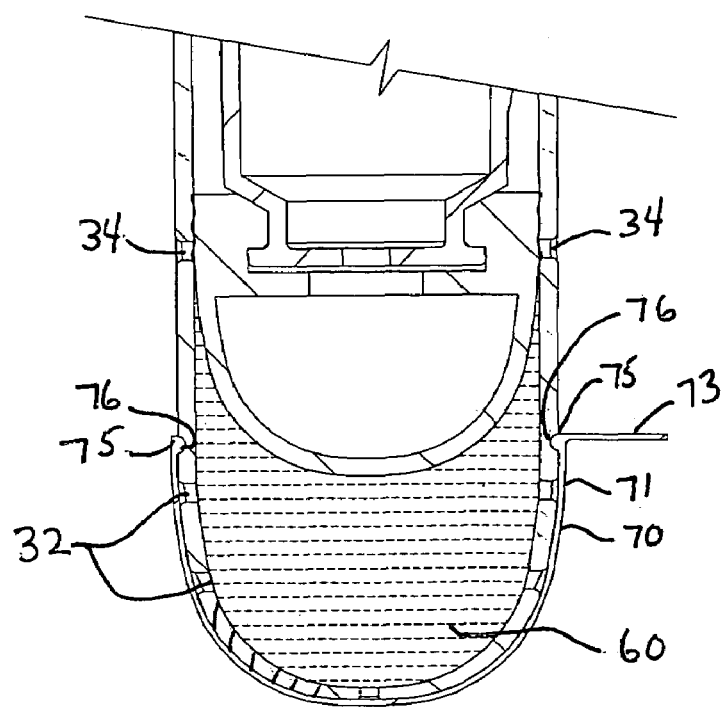
FIG. 3 is an enlarged view of the dispensing zone of an applicator within the scope of the present invention having a removable cover positioned on the exterior surface of the dispensing zone of the applicator.
Figure 4:
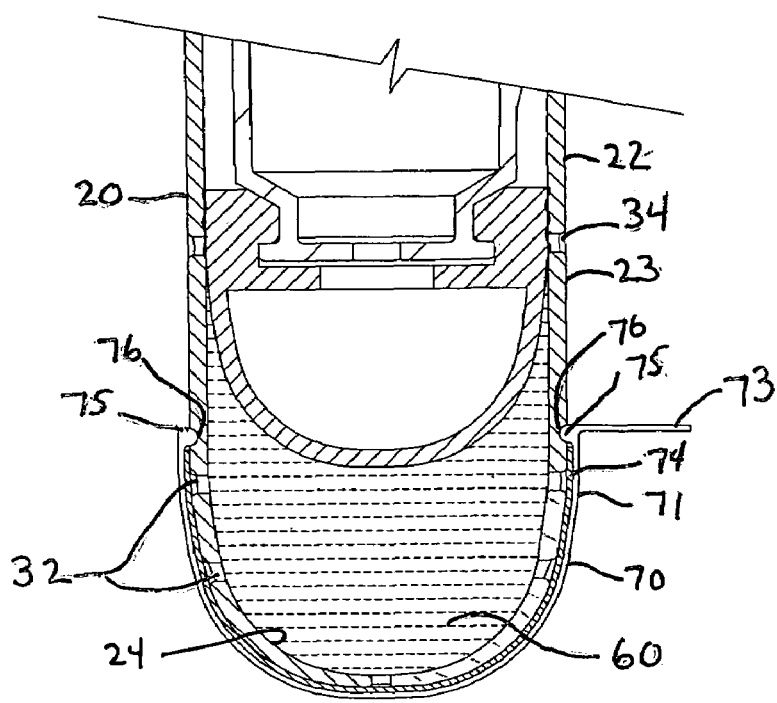
FIG. 4 is an enlarged view of the dispensing zone of an applicator within the scope of the present invention having a cover with a sealing member on an interior surface of the removable cover and the cover is positioned on the exterior surface of the dispensing zone of the applicator.

In the case where the removable cover 70 is a cap 71, attention is directed to FIGS. 3 and 4 which show a cap 71 positioned on the dispensing end 26 of the applicator. In FIGS. 3 and 4, the cap 71 has a gripping arm 73 which allows a user to grasp the gripping arm 73 to remove the cap 71 from the dispensing end 26 of the applicator 10 prior to use. In one embodiment of the present invention, shown in FIG. 4, the cap is also optionally provided with a sealing member 74 within the cap 71 such that the sealing member 74 is adjacent the exterior surface of the dispensing end 26 of the applicator when the cap 71 is applied to the applicator. Stated another way, the sealing means is between the exterior surface of the dispensing end 26 of the applicator 10 and the cap 71 or is located on the interior surface of the cap 71.

Any material which can effectively prevent or help prevent the therapeutic substance from being unintentionally removed from the chamber or reservoir 62 may be used as the foil, film or cap. The same is true for the sealing member 74 which lines the interior surface of the cap. Examples of foils and films include aluminum foils, polymeric films, such as polyethylene films, ethylene vinyl acetate and the like. Generally, the cap 71 is made from the same material in which the applicator 10 is prepared, due to ease of manufacturing considerations. As for the sealing member 74 located in the cap, suitable materials are rubber materials, such as silicone rubber, nitrile rubber and other similar materials. Optionally, to hold the cap 71 in place, the cap 71 and the exterior surface 23 of the first outer member 20 may have a detent feature, which includes a protrusion 75 on the interior surface cap 71 and a complementary recess 76 located on the exterior surface 23 of the first outer member 20. The protrusion 75 on the cap 71 may be around the entire interior surface of the cap 71 or located at certain locations. The same is true from the recess 76 located on the exterior surface 23 of the first outer member 20. This detent feature allows the cap 71 to be held in place prior to use and after use of the applicator. The optional detent feature helps prevent the cap 71 from becoming dislodged during storage, prior to use or after use.

In order to prevent the second inner member 40 from becoming pushed into the first outer member 20 prior to the intended use, the second inner member 40 and interior surface 24 of the first outer member 20 may be provided with an optional detent feature 50, which serves to hold the second inner member 40 in place prior to use. One example of the this detent feature 50 is shown in FIG. 2, which shows the interior surface 24 of the first outer member with a protrusion 51 and the second inner member 40 having a complementary indention 52. The protrusion is able to engage and be seated into the indention 52 so the second inner member 40 is not moved in relation to the first outer member 20 during storage and shipment. Movement of the second inner member 40 in relation to the first outer member 20 during shipment, storage or handling by a user may cause premature dispensing of the therapeutic substance 60 from the applicator. In the case where the second inner member moves in a direction away from the dispensing end 26 towards the distal end 28 of the second inner member, the therapeutic agent may leak from the aperture 34 located in the side wall 22 of the first outer member 20. In the case where the second inner member 40 is moved in a direction towards the dispensing end 26 of the first outer member 20, the therapeutic substance 60 may be prematurely ejected from the dispensing end 26. In either case, this could result in an insufficient quantity of the therapeutic substance 60 reaching the user, thereby ineffectively treating the symptoms of the user.

Another benefit of having a detent feature 50 is that the initial force to unseat the detent feature from its resting location may result in the therapeutic agent being ejected through the openings during use, which may result in greater coverage of the therapeutic substance in the place of use, such as the vagina of a user. Generally, with a detent feature 50 in place, the initial force to start the second inner member 40 moving towards the dispensing end 26 of the first outer member 20 is greater than the force to move the second inner member once the second inner member is unengaged from the detent feature 50.

Figure 5:
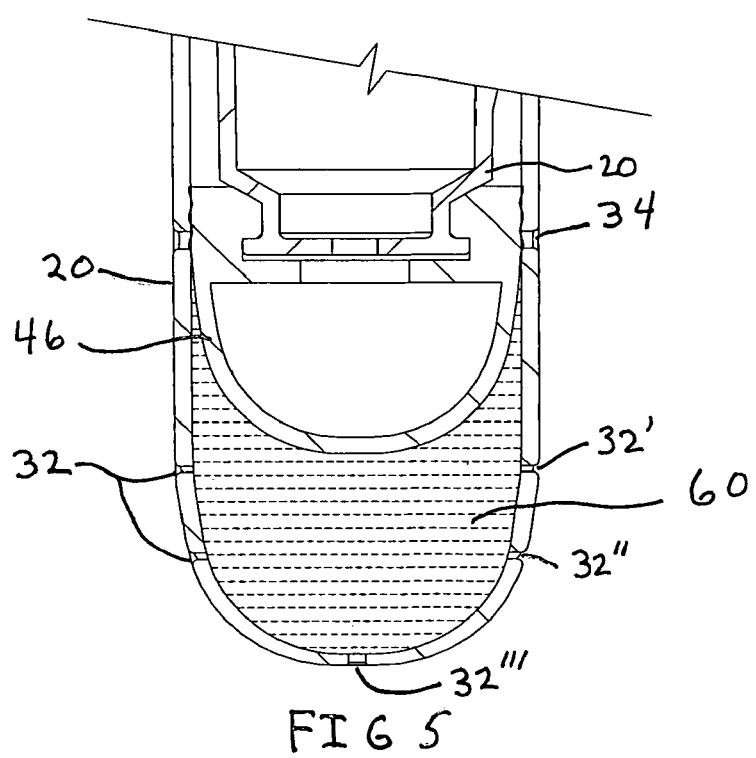
FIG. 5 is an enlarged view of the dispensing zone of an applicator within the scope of the present invention having graduated dispensing openings.

The openings 32 in the dispensing end 26 may be of uniform size or they may be graduated in size, as is shown in FIG. 5. As can be seen in FIG. 5, opening 32' is smaller in size than opening 32'', and opening 32'' is smaller in size than opening 32'''. Any configuration of size graduation may be used. For example, opening 32'' could be larger than both 32''' and 32', while 32' is larger than 32''' (not shown). By graduating the size of the openings, the flow of the therapeutic fluid may be equalized or designed to be concentrated at certain areas.

Figure 6:
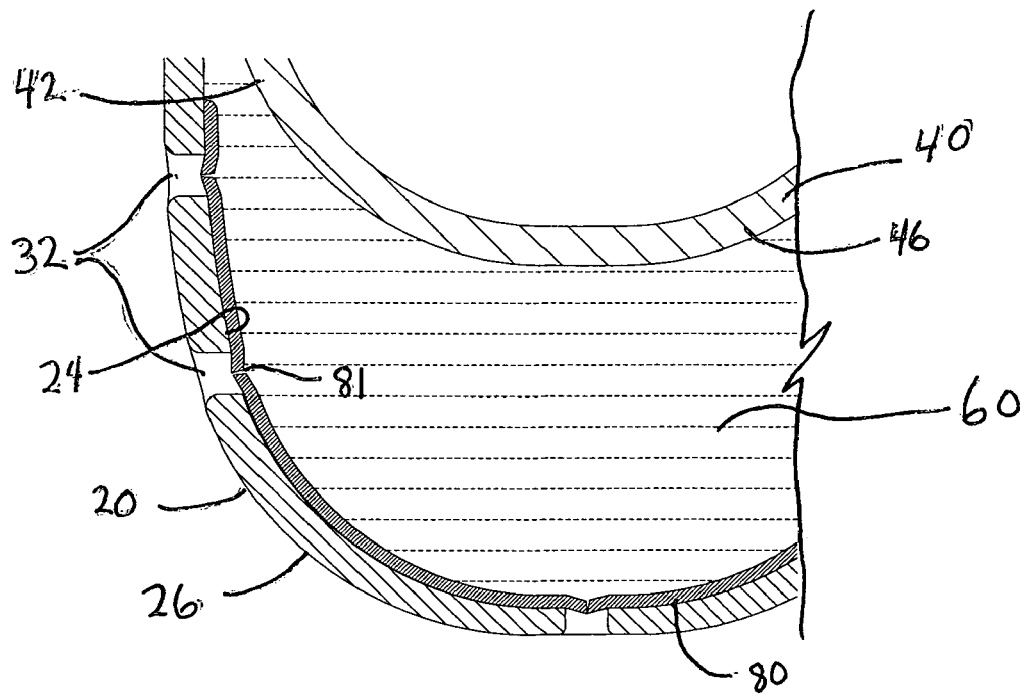
FIG. 6 is an enlarged view of the dispensing zone of an applicator within the scope of the present invention having an interior surface with a ruptureable sealing member.
Figure 7:
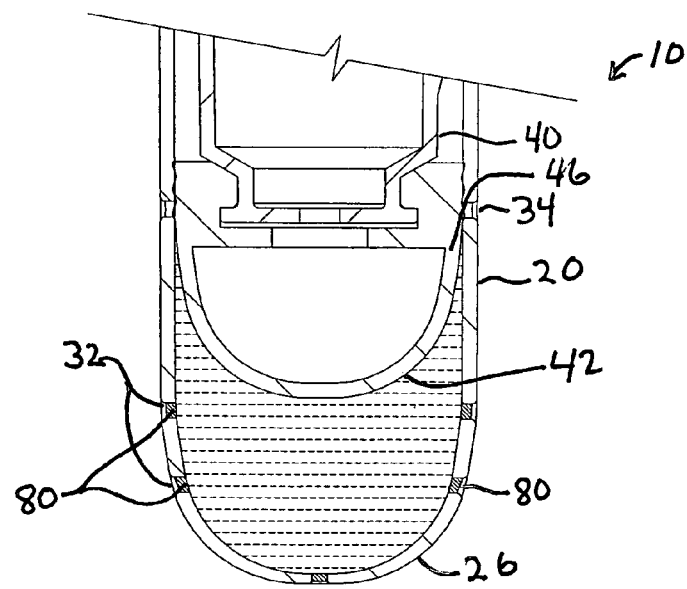
FIG. 7 is an enlarged view of the dispensing zone of an applicator within the scope of the present invention having a ruptureable seal within the openings in the dispensing zone of the applicator.
Figures 8A, 8B:
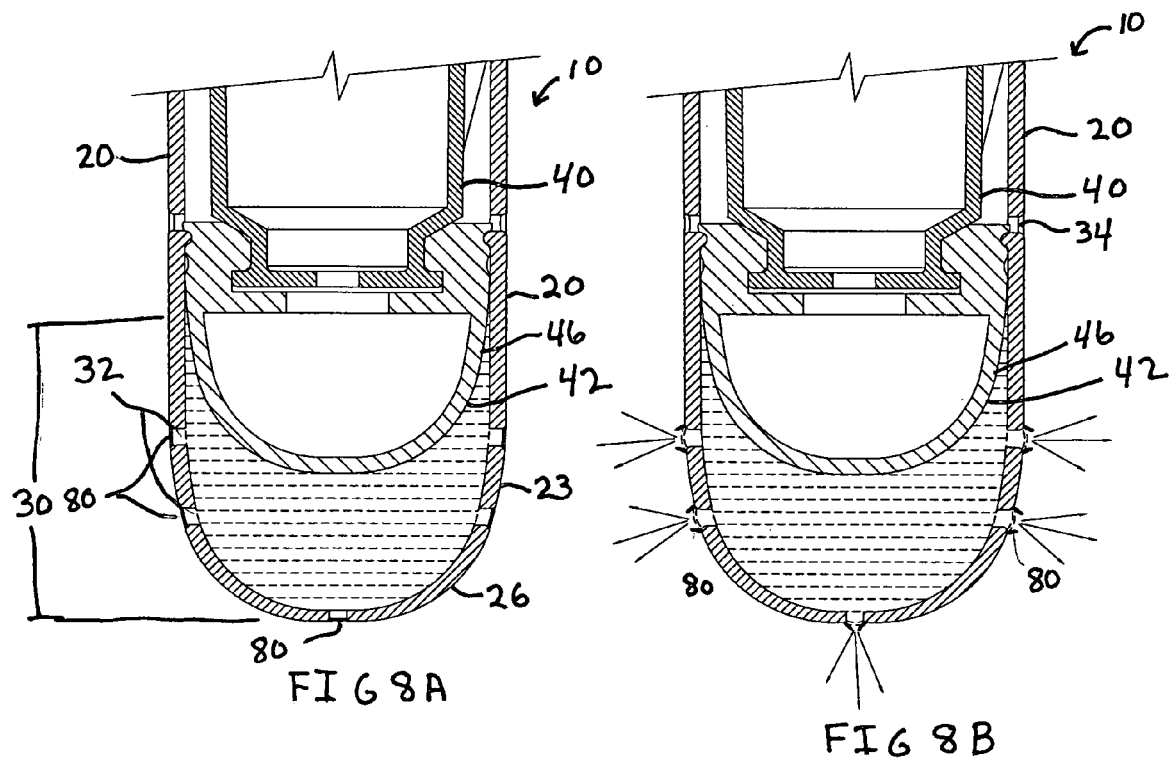
FIG. 8A is an enlarged view of the dispensing zone of an applicator within the scope of the present invention having an exterior surface with a ruptureable seal at the openings.
FIG. 8B is an enlarged view of the dispensing zone of an applicator within the scope of the present invention having an exterior surface ruptureable seal at the openings, showing the exterior surface ruptureable seal member rupturing to dispense the therapeutic substance from the chamber of the applicator.

As is described above, the applicator 10 of the present invention may be provided with a removable cover 70 on the dispensing end of the applicator 10, which may prevent leaks from the applicator 10. In addition to this removable cover, or in place of the removable cover, the dispensing end 26 of the first outer member of the applicator may be provided with a ruptureable seal 80. The ruptureable seal. 80 may be located on the interior surface 24 of the first outer member 20, as is shown in FIG. 6. Alternatively, the ruptureable seal 80 may be located within the openings 32, as is shown in FIG. 7, or on an exterior surface 23 of the outer first member 20, as is shown in FIG. 8A. In any case, the ruptureable seal 80 closes the opening 32, which may prevent the therapeutic substance 60 from leaking from the applicator or being dispensed prematurely. In each case, the ruptureable seal is ruptured upon the application of force on the therapeutic substance 60 by plunger tip 46 or proximate end 42 of the second inner member 40. That is, when a force is applied to the distal end 44 of the second inner member 40, this force is applied to the therapeutic substance 60, which in turn applies the force to the ruptureable seals and the dispensing end 26 of the first outer member. This force causes the ruptureable seals 80 to break or become dislodged from the openings 32.

In the case where the ruptureable seal 80 is located on the interior surface 24 of the dispensing end 26 of the first outer member, as is shown in FIG. 6, generally the ruptureable seal 80 will have a pin hole 81 located in the ruptureable seal 80. Suitable materials which may be used to make the ruptureable seals shown in FIG. 6 include rubber materials or film materials. One particular material which may be used is a silicone rubber. Silicone rubbers often exhibit a "self healing" function, which will allow the therapeutic substance 60 to be expelled from the applicator when pressure is applied to the second inner member 40 towards the first outer member 20. Typically, with the pin hole 81 in the silicone rubber, the silicone rubber will distort when the pressure is applied, as is shown in FIG. 6. When the pressure is no longer asserted, the silicone rubber will tend to close the opening by returning to its undistorted position, which will form an effective seal to prevent the therapeutic agent from escaping from the applicator 10.

As is shown in FIG. 7, the ruptureable seal 80 is located within the openings 32 of the dispensing end 26 of the applicator 10. When a force is applied to the therapeutic agent by the distal end 44 or plunger tip 46 of the second inner member, this force is transferred to the ruptureable seal 80 located within the openings 32. This causes the ruptureable seal 80 to become dislodged from the openings 32, forcing the seal material out of the openings. In the case of a ruptureable seal which is dislodged from the openings, the ruptureable seal 80 will be expelled into the body of the user or patient. As a result, the dislodgeable ruptureable seals should be made from materials that are acceptable by the body or can be processed by the body of a user or patient. Examples of such materials include waxes, natural materials or any other material which may be processed by the body of the patient or user, without causing irritation or other complications to the patient or user of the applicator. In the case of waxes, typically the body temperature will cause the wax to melt and be expelled from the body.

As is shown in FIG. 8A, the ruptureable seal 80 may be located on the exterior surface 23 of the dispensing zone 30 of the applicator 10. The ruptureable seal 80 may be a thin film or membrane. The ruptureable seal on the exterior surface may be made from the same material used to prepare the first outer member 20, or may be another material applied to the exterior surface 23. In this embodiment, when a force is applied to the therapeutic agent by the distal end 44 or plunger tip 46 of the second inner member 40, this force is transferred to the first outer member 20 and the ruptureable seal 80 located at the openings 32. Since the ruptureable seal 80 is a thin and relatively weak material as compared to the first outer member, the ruptureable seal 80 will break and allow the therapeutic agent 60 to be dispensed from the applicator, as is shown in FIG. 8B.

As is stated, above, the ruptureable seal 80 may be used in combination with removable cover 70 or in place of the removable cover. It is also noted that the ruptureable seal 80 need not be used, if the openings 32 in the first outer member 20 are of a sufficiently small size that the openings themselves are capable of keeping the therapeutic substance 60 in the chamber or reservoir 62.

To prepare the applicator of the present invention, first the first outer member 20 is provided. The first outer member 20, having the vent aperture 34 and the openings 32 in the dispensing end, is prepared and provided to the manufacturing process. The openings in the dispensing end are covered in a manner described above, such as with a removable cover, a ruptureable seal or a combination thereof. The removable cover may be affixed to the first outer member 20 using any number of adhesives or sealants. The removable cover and/or ruptureable seal must cover all of the openings or apertures in the dispensing end 26, except the vent holes or aperture 34 located in the side wall of the first outer member 20, shown for example in FIGS. 2-8A. Once the first outer member 20 has all of the openings 32 at the dispensing end sealed, the therapeutic substance is dispensed into the interior volume of the first outer member. After dispensing the therapeutic substance into the first outer member 20, the second inner member 40 is inserted and pressed into the first outer member 20, as is shown in FIG. 1. As the second inner member 40 is inserted into the first outer member 20, the apertures 34 allow air or other gases trapped between the second inner member 40 and the first outer member 20 to escape. The air or gas inside the first outer member is displaced by the second inner member 40 as the second inner member 40 moves towards the dispensing end 26 of the first outer member 20. The second inner member 40 is pressed into the first outer member 20 until the integral seals on the second inner member or plunger tip 46 seal off the apertures 34 or the second inner member engages the detent feature, if present. Generally, it is recommended that the volume of therapeutic substance, the inner tube insertion distance, the position of the apertures 34, and the position of the 0 seals or the plunger tip 46 of the second inner member be selected in such a way that insertion of the second inner member does not result in displacing medication through the apertures 34. Once the components are assembled, the syringe is packaged in a hermetically or otherwise sealed pouch and placed in cartons. The cartons are transferred to warehouses or directly to the place of use or other supply facilities.

Figures 9A, 9B:
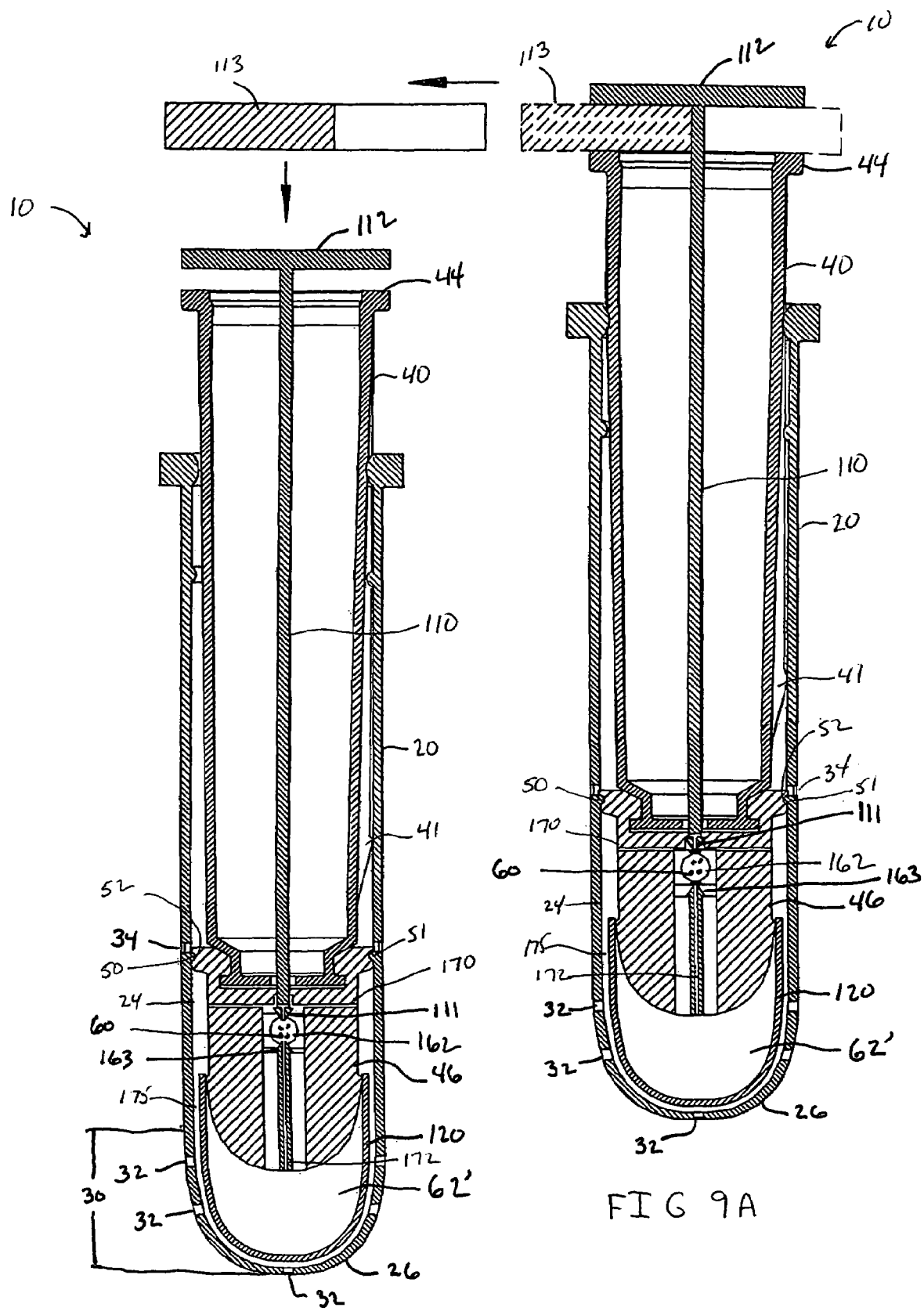
FIG. 9A shows another embodiment of an applicator of the present invention which is capable of dispensing a solid or powdered therapeutic substance.
FIG. 9B shows the embodiment of FIG. 9A where the piercing points engage the therapeutic substance chamber to allow the therapeutic substance to be released from the chamber and the applicator.

In another embodiment of the present invention, the applicator 10 may also be adapted to deliver solid or powder-like therapeutic agents. In this regard, attention is directed to FIGS. 9A and 9B. In this configuration, the applicator 10 has a first outer member 20 having a shape suitable for insertion into a body cavity of a subject. The applicator 10 also has a second inner member 40, which is coaxially and slidably housed within the first member 20. Within the second inner member 40 is a third member 110, which extends along the longitudinal axis LA of the applicator 10. As is shown in FIG. 9A, the second inner member 40 is located within the first member 20 and the third member 110 is located within the second inner member 40 along the longitudinal axis LA. The third member 110 has a first end 111 which contacts with a therapeutic agent chamber 162 containing the therapeutic substance 60. The third member 110 has a second end 112, which may extend beyond the second end 44 of the inner or second inner member 40. The second end 112 of the third member 110 serves as a place for a user to apply force to the third member 110 to activate or release the therapeutic substance 60 from the therapeutic agent chamber 162.

The first end 111 of the third member generally has a piercing or lancing mechanism, such as a point as shown in FIG. 9A, which will pierce or lance the therapeutic agent chamber 162, thereby allowing the release of the therapeutic agent 60 from the therapeutic agent chamber 162. Generally, as is shown in FIG. 9A, the third member 110 is seated in the second inner member near the plunger tip 46 of the second inner member 40. The therapeutic agent chamber 162 may be located within the plunger tip 46 of the second inner member 40 or may be located within an inner chamber 62'. The inner chamber 62' is formed by an inner chamber member 120 and the plunger tip 46 of the second inner member 40. The inner chamber member 120 is generally formed when the first outer member 20 is formed and may be integral with the first outer member 20. Alternatively, the inner chamber member 120 may be a separate material which is inserted into the interior portion of the first outer member 20 and held in place by a suitable mechanism, such as an adhesive. Generally, the plunger tip 46 of the second inner member 40 and the inner chamber member 120 are in a fluid tight relationship to one another, whereby a portion of the plunger tip 46 contacts the inner chamber member 120. By fluid tight relationship, it is meant that a fluid, such as a liquid or gas, will not easily escape from the inner chamber 62' between the inner chamber member 120 and the portion of the plunger tip 46 of the second inner member 40 which contacts the inner chamber member.

The plunger tip 46 of the second inner member 40 may also have a piercing or lancing mechanism 163 which will serve to pierce or otherwise break the therapeutic agent chamber 162. The piercing or lancing mechanism 163 may be a structure which comes to a point adjacent the therapeutic agent chamber 162, as shown in FIG. 9A, or may be a flat surface which holds the therapeutic agent chamber 162 in place so that the first end 111 may pierce or lance the therapeutic agent chamber 162 to release the therapeutic agent 60. As is shown in FIG. 10, the piercing or lancing mechanism 163 may be a structure that has a channel 172 therein, which will effectively allow a fluid or gas in the inner chamber 62' to be passed into the therapeutic agent chamber 162, which will in turn cause the therapeutic agent to be entrained in the fluid or gas passing through the therapeutic agent chamber 162.

As with the first embodiment of the present invention, the first outer member 20 has a dispensing end 26 having a dispensing zone 30 with one or more openings 32 which allow the therapeutic substance 60 to be administered to a body cavity of the subject in need of treatment with the therapeutic substance. In addition, the first outer member 20 has one or more apertures 34 which allow air or gases to escape the applicator during manufacture of the applicator 10. In order to prevent the second inner member 40 from becoming pushed into the first outer member 20 prior to the intended use, the second inner member 40 and interior surface of the first outer member may be provided with an optional detent feature 50, which serves to hold the second inner member 40 in place prior to use. One example of this detent feature 50 is shown in FIG. 9A, which shows that the interior surface 24 of the first outer member with a protrusion 51 and the second inner member 40 having a complementary indention 52, in which the protrusion is able to engage and be seated therein. This will result in the second inner member 40 being held stationary in relation to the first outer member 20 during storage and shipment. Essentially, any and all of the features of the first embodiment of the present invention may be present in the embodiment of the present invention shown in FIG. 9A. For example, the applicator 10 of FIG. 9A could optionally have a removeable cover placed on the dispensing end 26 of the first outer member 20, or the plunger tip 46 could have O-rings or seals present where the plunger tip 46 of the second inner member 40 contacts the interior surface 24 of the first outer member 20 or the plunger tip 46 contacts inner chamber member 120.

In the embodiment of the present invention shown in FIG. 9, there are other features present. One of these features is the plunger tip 46 of the second inner member 40 is provided with a channel 170, which allows the therapeutic substance 60 to be transferred from the pierced, lanced or broken therapeutic substance chamber 162 to a channel 173. Channel 173 is created by the plunger tip 46 and the inside surface 24 of the first outer member. Channel 175, which is connected to channel 173, is created by the inner chamber member 120 and the inside surface 24 of the first outer member 20. Another feature is retainer 113, which is placed between the second end 112 of the third member and the second end 44 of the second inner member 40. The retainer 113 is removable prior to use and keeps the third member 110 and the second inner member 40 in a relationship to one another such that the third member 110 is kept from being moved in a direction towards the therapeutic agent chamber 162 prior to intended use, which prevents the therapeutic agent chamber 162 from becoming pierced, lanced or broken prior to intended use.

The therapeutic agent chamber 162 may be made from any material which may be pierced, lanced or otherwise broken when a force is applied to the second end 112 of the third member 110 towards the therapeutic agent chamber. Suitable materials include polymeric materials, wax materials and the like. Biocompatible polymers are preferred, such as polyvinyl alcohol, polyvinyl acetate and the like. The material selected should be such that if any of the therapeutic agent chamber 162 is released from the applicator.10, it should not be harmful to the user or patient being treated with the applicator.

To use applicator 10 shown in FIG. 9A, the retainer 113 is first removed from the applicator 10 as is shown in FIG. 9A and 9B. Next, the second end 112 of the third member 110 is pushed in a direction towards the second inner member 40 and the therapeutic agent chamber 162, as is shown in FIG. 9B. This will cause the therapeutic agent chamber 162 to be compromised, such that the therapeutic substance 60 in the chamber 162 will be released or releasable from the chamber 162. The second end 44 of the second inner member 40 is push into the first outer member 20 which causes the plunger tip 46 to move inward to the dispensing end 26 of the first outer member. As is shown in FIG. 10, the plunger tip 46 is in a fluid tight relationship with the inner chamber member 120, which causes any air, gas or other fluid within the inner chamber 62' to be expelled from the inner chamber 62', and passes the therapeutic agent 60 in the therapeutic agent chamber 162. As the gas or fluid passes through the therapeutic agent chamber, the gas or fluid picks up or entrains the therapeutic agent 60 and travels through the channel 170 in the plunger tip to the channel 173, then to the channel 175 and out of the openings 32, as is shown by the pathway 199 in FIG. 10. As a result, a powdered therapeutic agent 60 of FIGS. 9A, 9B and 10 is administered to the user or subject in need of the therapeutic substance.

As an alternative to having the therapeutic agent located in the chamber 62, as is shown in FIGS. 11 and 12, the therapeutic agent 60 may be located in the plunger tip 46 of the second inner member 40. In FIG. 11, the therapeutic agent is located within a plunger tip chamber 262 in the plunger tip 46. The interior surface 24 of the first outer member 20 is provided with a piercing mechanism 261 which will pierce a seal 263 located in the plunger tip chamber 262 of the plunger tip. The piercing mechanism 261 serves to break the seal 263 to release the therapeutic substance 60 from the plunger tip 46 into the chamber 62. As the second inner member 40 is compressed against the interior surface 24 of the dispensing end 26, the therapeutic substance 60 is released from applicator 10 through the openings. Similarly, as shown in FIG. 12, the therapeutic substance 60 is placed within a liquid filled bag 265, which is pierced by a piercing mechanism 261 to release the therapeutic substance 60 from the filled bag. In FIG. 12, as the second inner member 40 is compressed against the interior surface 24 of the dispensing end 26, the therapeutic substance 60 is released from applicator 10 through the openings 32.

Figure 13:
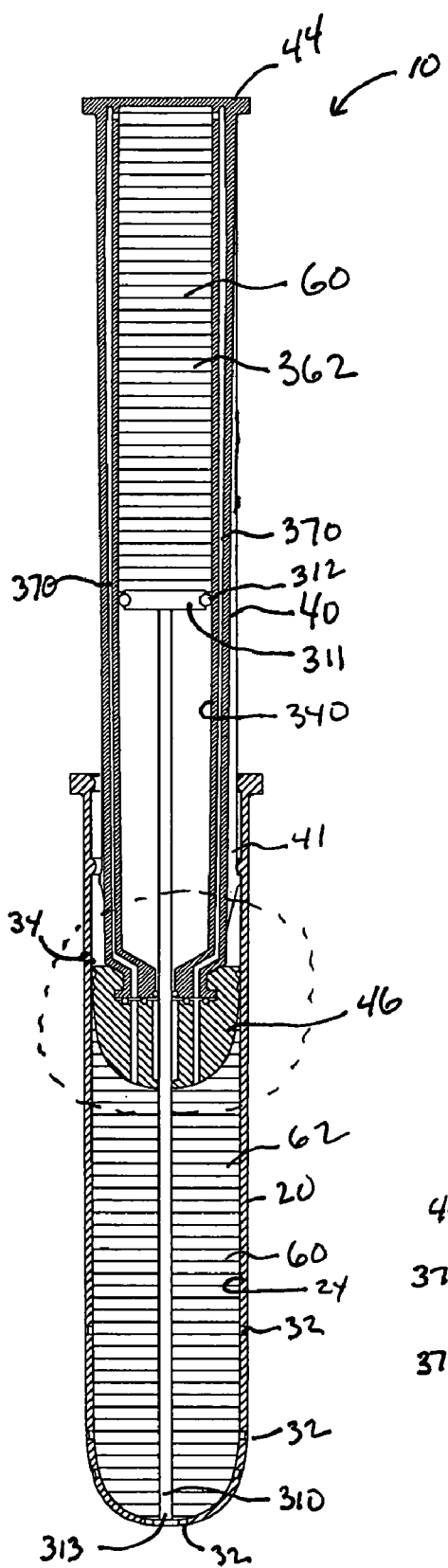
FIG. 13 shows a further embodiment of the present invention with an additional reservoir of the substance to be administered present in the second inner member of the applicator within the scope of the present invention.

In a further embodiment of the present invention, an applicator having a higher capacity is shown in FIG. 13. The higher capacity applicator 10' has essentially all of the features of the applicator 10 shown in FIG. 1, but second inner member 40 has a second chamber or reservoir 362 of the therapeutic substance 60. The chamber or reservoir 62 is connected to the second chamber or reservoir 362 by a series of channels 370 in the second inner member 40 and the plunger tip 46 of the second inner member. To release the therapeutic substance 60 from the second chamber 362, a piston 310 may be attached to the interior surface 24 of the first outer member 20 at a location at or near the dispensing end 26 of the first outer member. The first end 311 of the piston 310 is located in the second inner member 40. To ensure that the therapeutic substance 60 does not escape by the piston 310, seals 312 are placed at the first end 311 of the piston. The seals 312 contact the interior surface 340 of the second inner member 40. The second end 313 of the piston 310 may be attached to the interior surface 24 or otherwise held in place in relationship to the first outer member 20.

Figure 13A:
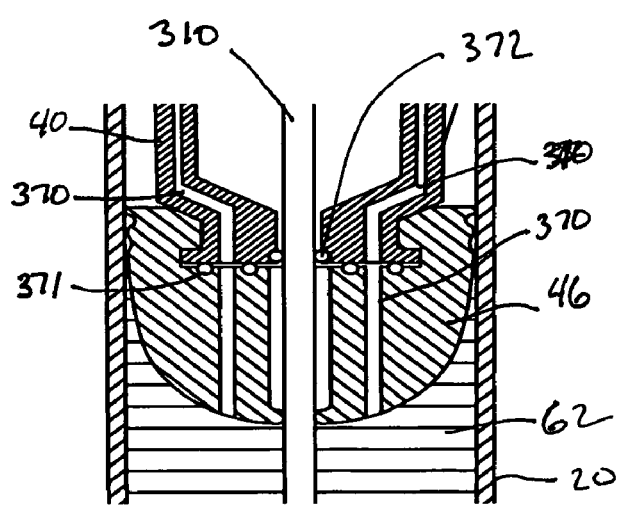
FIG. 13A shows an enlarged version of the encircled portion of FIG. 13.

Still referring to FIG. 13, the channels 370 in the second inner member 40 are located between the exterior surface 341 of the second inner member 40 and the interior surface 340 of the second inner member 40. The channels 370 extend into and through the plunger tip 46 of the second inner member 40 and into the chamber or reservoir 62. When the second inner member 40 is a two-piece second inner member, as is shown in FIG. 13A, where the plunger tip 46 joins the remainder of the second inner member 40, seals 371 may be present to prevent leaking, if needed. In addition, other seals 372 may be present on the second inner member 40 where the piston 310 goes through the plunger tip 46.

As the second inner member 40 is pushed from the second end 44 towards the first outer member 20, the piston 310 remains stationary, thereby forcing the therapeutic substance 60 from second chamber or reservoir 362 into the channel 370 and into the chamber or reservoir 62. The therapeutic substance 60 is forced out of the openings 32 and into the subject being treated with the applicator. The higher volume applicator shown in FIG. 13 is useful in applications such as douches or cleansing applications that require a higher volume of the therapeutic substance.

In the application of some therapeutic agents, it is desirable to treat a larger surface of the vaginal canal. However, the length of the vaginal canal being treated is partially dictated by the volume of liquid in the end of the applicator. As a result, if it is necessary to treat more area with the same amount of fluid, an additional means to achieve this objective is needed. The embodiments of the present invention shown in FIGS. 14 and 15 help make the length of the vaginal canal being treated independent of the volume of therapeutic agent being dispensed from the applicator.

Figure 14:
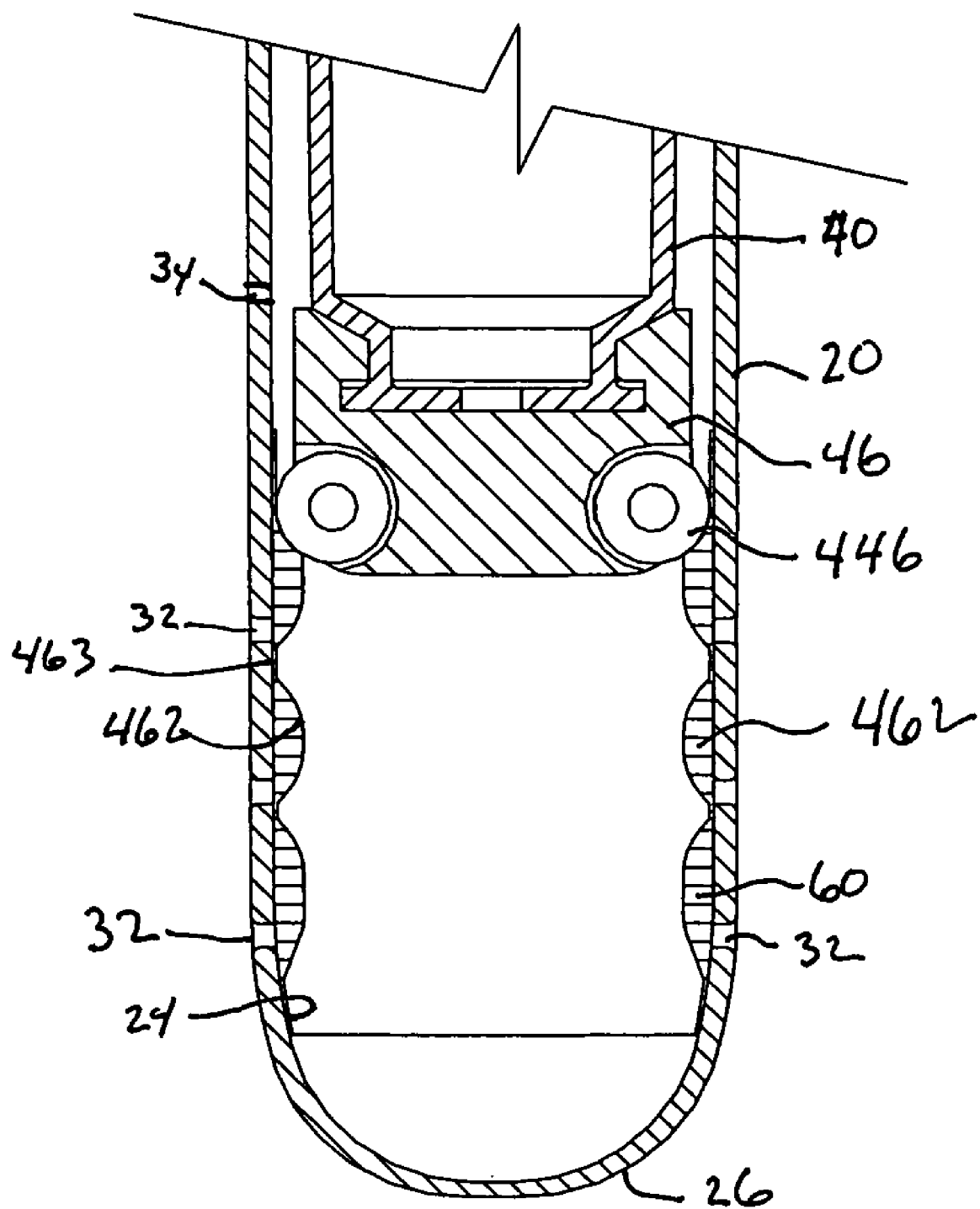
FIG. 14 shows an embodiment of the present invention wherein the substance to be administered is stored in pockets on the interior surface of the first outer member.

In another alternative embodiment of the present invention, which is shown in FIG. 14, the therapeutic substance 60 is stored in pockets or bags 462 which are positioned on the interior surface 24 of the first outer member 20. In this embodiment of the present invention, the pockets or bags 462 are positioned over the openings 32. As the second inner member 40 is pushed into the first outer member 20, the plunger tip 46 of the second inner member crushes the pockets or bags 462, forcing the therapeutic substance 60 from the bags or pockets 462 and through the openings. The plunger tip may have many configurations, but to ensure uniform crushing of the bags or pockets 462, the plunger tip may be mounted with rollers 446, which serve to crush the bags or pockets. Generally, each bag or pocket 462 has at least one opening to allow the therapeutic agent escape from each bag or pocket 462.

In the embodiment of the present invention shown in FIG. 14, the bags or pockets 462 may be formed from a flat sheet of a film. The bags or pockets 462 have seals 463 between the individual bags or pockets 462 which isolates the contents of each bag or pocket 462 from the others, which results in the therapeutic agent being more evenly dispensed in the place of application and may prevent pooling in the place of application where a gap may be present. The first outer member 20 with the bags or pockets may be formed by forming a film on the interior surface 24 of the first outer member 20.

Figure 15:
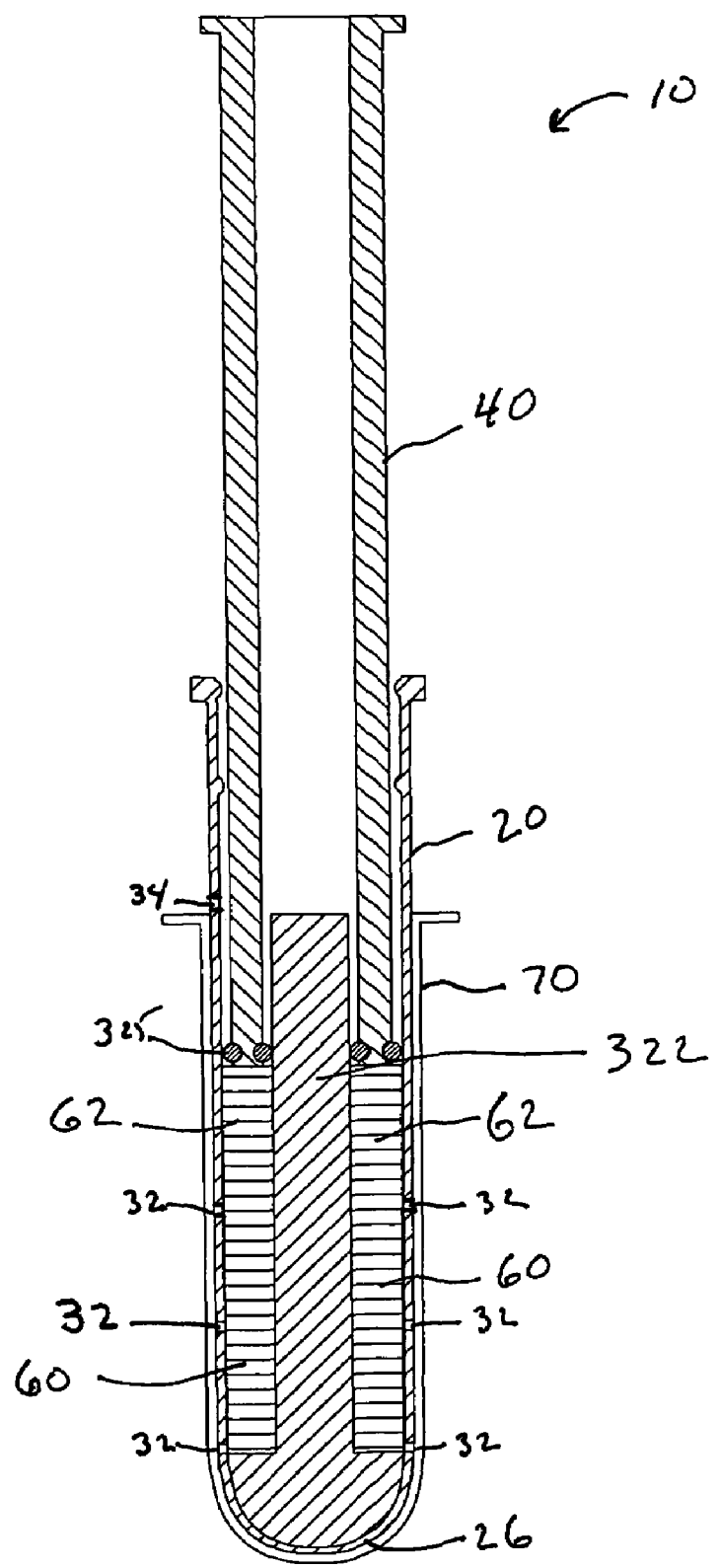
FIG. 15 shows an embodiment of the present invention where a displacement member is inserted into the first outer member of the applicator.

In FIG. 15, a displacement member 322 is positioned in the first outer member 20 so that the volume of the chamber or reservoir 62 may be reduced. Typically, in this embodiment of the present invention, the second inner member 40 will have seals 325 located where the second inner member 40 meets the displacement member 322 and the interior surface 24 of the first outer member 20. As is mentioned above, by placing the displacement member 325 in the first outer member 20, the same volume of therapeutic agent 60 may be administered over a larger area as compared to an applicator without a displacement tube.

Figure 16:
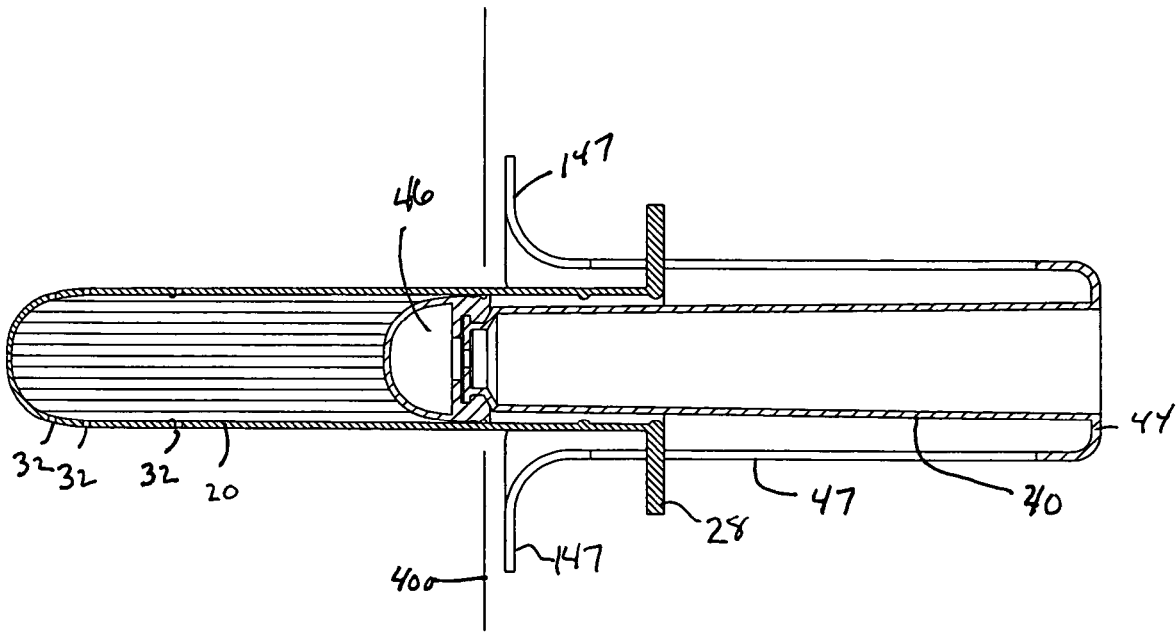
FIGS. 16A and 16B show an embodiment of the present invention where a shroud is placed over the second inner member.
Figure 16B:
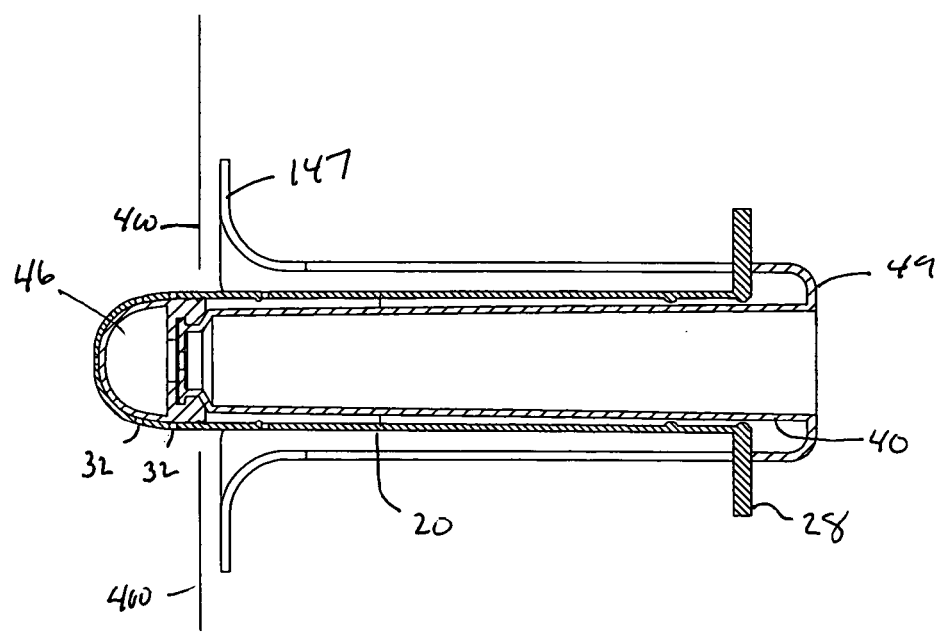

As is mentioned above, in the application of some therapeutic agents, it is desirable to treat a larger surface of the vaginal canal. One way to increase coverage, if the volume of the therapeutic agent is not an issue, is to increase the number of openings in the first outer member. However, with more openings, it is possible that the therapeutic agent may leak from the applicator before application. One way to keep the number of openings to a minimum while still providing maximum coverage is to have the first outer member 20 move along the treatment area as the therapeutic substance is dispensed. One way to accomplish this is shown in FIG. 16A, which is to provide the second inner member 40 with a shroud 47. The shroud extends over the second inner member 40 and has a flange 147, wherein the flange rests against the user's body 400. When the distal end 44 of the second inner member 40 is pushed and the second end 28 of the first outer member 20 is pulled, the first outer member 20 is caused to be removed from the user's body, as is shown in FIG. 16B. As a result, a larger area of a user's body cavity may be treated with fewer openings in the first outer member.

Any therapeutic substance may be used in the applicator 10 of the present invention. The therapeutic substances generally include a therapeutic agent, along with any excipients, compounds, or other ingredients that are desirable to introduce into the vaginal or other cavity to promote the functionality of that therapeutic agent. The excipients may assist the release of the therapeutic agent, or assist in the absorbency of the therapeutic agent into the vagina or other epithelium. The use of excipients to facilitate the formulation, delivery, stability, and aesthetic properties of a therapeutic agent delivery system is well known to those familiar with the art. Examples of ingredients that may accompany the therapeutic agent include excipients, biologically-compatible adhesives, surfactants, and penetration enhancers. An example of a suitable excipient is SUPPOCIRE suppository base, available from Gattefossé Corp. SUPPOCIRE suppository base is a semi-synthetic glyceride. An example of a suitable biologically-compatible adhesive is hydroxypropyl methylcellulose (HPMC), available as METHOCEL K15M from The Dow Chemical Company. An example of a suitable surfactant is polysorbate 80, available from Spectrum Chemical Manufacturing Corp. An example of a suitable penetration enhancer is LABRAFIL M 1944 C nonionic amphiphilic excipient, available from Gattefossé Corp.

For the purposes of this invention, any therapeutic agent that will treat the vaginal or other cavity, other mucosal tissue, or will be absorbed into a user's body through the vagina or other epithelium for the purposes of treating diseases or conditions, promoting the growth of normal vaginal bacterial flora, or promoting vaginal health may be used. Examples of therapeutic agents include but are not limited to vitamins, minerals, hormones, moisturizers, antifungal agents, antibacterial agents, pro-biotics, botanicals, analgesics, prostaglandin inhibitors, prostaglandin synthetase inhibitors, leukotriene receptor antagonists, essential fatty acids, sterols, anti-inflammatory agents, vasodilators, chemotherapeutic agents, and agents to treat infertility.

Some therapeutic agents for use in this invention are absorbable through the vaginal epithelium and travel to the uterus by a unique portal of veins and arteries that are known to exist between the vagina, the cervix, and the uterus. This anastomosis eliminates first-pass metabolism by the liver, effectively delivering higher concentrations of the therapeutic agent to the uterus than would otherwise be available via oral dosing. Those of skill in the art know the efficacy of various therapeutic agents when introduced at a particular anatomical location. For example, when the therapeutic agent is selected to treat dysmenorrhea, it preferably is selected from the following group: nonsteroidal anti-inflammatory drugs (NSAIDs), prostaglandin inhibitors, COX-2 inhibitors, local anesthetics, calcium channel blockers, potassium channel blockers, β-adrenergic agonists, leukotriene blocking agents, smooth muscle inhibitors, and drugs capable of inhibiting dyskinetic muscle contraction.

Alternatively, therapeutic agents modify the vaginal or other environment to enhance the wellness of this anatomical region. The benefits may be rather simple, for example increasing comfort by providing moisturization and/or lubricity. These benefits may also be more complex, for example modulating epithelial cell function to address vaginal atrophy. The beneficial therapeutic agents may reduce negative sensations such as stinging, burning, itching, etc, or introduce positive sensations to improve comfort. The therapeutic agent delivered by the applicator of the present invention need not be a "medication" per-se. It could also be a vaginal cleansing product, deodorant douche, lubricant, spermicidal cream, afrodesiac, pH balancing liquid, just to name a few.

Also as can be seen in Figures of the present invention, the applicator 10 is shown to have an outward appearance which is a generally cylindrical shape. That is, the first member is an elongated tube having a generally cylindrical shape. By having this generally cylindrical shape, the applicator 10 takes the appearance of a conventional tampon applicator, such as a Kotex® Security® Tampon, as well as other commercially available tampons. As a result of this outward appearance, the use of the applicator 10 of the present invention is more intuitive to a user as compared to some of the previously available applicators, which take a more syringe-like appearance. Further, by the size, shape and appearance of the applicator, a user will not be as intimidated by the applicator during use, as compared to an applicator having a syringe-like appearance, since users who use applicator-type tampons will be fairly familiar with the use of the applicator shown in the figures of the present invention. As a result, the applicator of the present invention may be easier to use for a user, as compared to an applicator with a syringe-like appearance.

In addition, the applicator of the present invention works like a syringe and, therefore, the medication is in the form of a liquid, cream, foam, or powder. Outwardly, the applicator looks like a conventional Kotex® Security® Tampon, or other commercially available tampon applicators, and is inserted into the body in the same way as an applicator tampon is inserted into the body. The first outer member looks like the first outer member of a Kotex® Security® Tampon, or other commercially available tampon, minus the petals. The outer tube has holes towards the rounded end of the tube in place of the petals. The only difference in the use of the applicator of the present invention is that when the distal end 44 of the second inner member 40 is pressed, the applicator dispenses a therapeutic substance.

If a therapeutic agent is needed during menstruation, this applicator of the present invention would typically be used without a tampon being inserted in the vagina of a user. This has the benefit of minimizing issues with a tampon absorbing the medication before it can be absorbed into the body. Once the medication is administered, the woman has the option of using a tampon or a feminine pad to absorb menstrual flow. This applicator of the present invention has the further benefit of not forcing women to use a tampon when they need medication while menstruating.

This applicator of the present invention may be used by point-of-care heath care professionals at a hospital or clinic or it can be prescribed by a physician and used by the patient in the comfort of their own home. Most women today are familiar with tube applicator tampons and are not intimidated by their use. Given women's prior familiarity with using tube applicator tampons, little or no education is necessary on how to insert and use the device. This would facilitate the transition of this product from a prescription to over-the-counter marketing, and it would facilitate the marketing of products in non-prescription markets without the need to educate users on how to use the product, beyond the basic usage.

This applicator of the present invention is primarily a woman's health and hygiene product. However, it could also be adapted for use in the rectal delivery of medications for use in hospitals or homes. A very small device like this could be made for the rectal delivery of medications in infants and children. The benefit of using an applicator to administer medication is cleanliness and convenience since the medication does not need to be touched by the caregiver.

To use the applicator of the present invention, the user or care giver removes the applicator 10 from the sealed pouch. If a removeable cover 70 is present, the user or care giver will remove the removeable cover 70. Next, the applicator 10 is inserted into the desired treatment location, for example the vagina, and a force is placed on the distal end 44 of the second inner member 40 to displace the therapeutic substance from the chamber or reservoir 62 into the treatment locations. Once inserted and the active substance is dispensed, the applicator is removed and disposed of in an environmentally friendly manner.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

We claim:

1. An applicator for introducing a therapeutic substance into a body cavity of a subject, said applicator comprising:
   a. a first outer member having a shape suitable for insertion into a body cavity of a subject, the first outer member comprising at least one side wall, an interior surface, a first dispensing end and a second end distal to the dispensing first end wherein the dispensing end of the first outer member has a dispensing zone comprising at least one opening and the at least one side wall joins the first dispensing end of the first outer member to the second end;
   b. a second inner member having a proximate end and a distal end, the second inner member being coaxially and slidably housed within the first outer member such that the proximate end of the second inner member is within the first outer member, and the distal end of the second inner member extends beyond the second end of the first outer member; and
   c. at least one non-dispensing aperture located in the side wall of the first outer member, wherein the aperture is located at a position on the side wall of the first outer member between the dispensing zone and the second end of the first outer member further comprising a third member,
   said third member extends along a longitudinal axis of the applicator and is housed within the second inner member,
   the third member comprising a first end which is adjacent a therapeutic agent chamber containing a therapeutic agent,
   wherein the third member is disposed entirely outside of the therapeutic agent chamber, a second end which extends beyond the distal end of the second inner member, wherein the first end of the third member is adapted to pierce, lance or break the therapeutic agent chamber when the second end of the third member is moved in along the longitudinal axis towards the second inner member.

2. The applicator according to claim 1, wherein the first outer member comprises an elongated tube having a generally cylindrical shape.

3. The applicator according to claim 1, wherein the at least one aperture is located on the side wall of the first outer member proximate to the dispensing zone of the first outer member.

4. The applicator according to claim 1, further comprising a removable cover which covers the at least one opening in the dispensing zone of the first outer member.

5. The applicator according to claim 4, wherein the removable cover comprises a foil, a film, or a cap.

6. The applicator according to claim 1, further comprising a chamber, said chamber is located at or adjacent to the dispensing end of the first outer member, the chamber being defined by a volume created by the interior surface of the first outer member located at or near the dispensing end of the first outer member and the proximate end of the second inner member, said chamber being adapted to hold a therapeutic substance to be introduced into the body cavity by said applicator.

7. The applicator according to claim 6, wherein the chamber contains a therapeutic substance.

8. The applicator according to claim 7, wherein the therapeutic substance comprises a medicament.

9. The applicator according to claim 8, wherein in the medicament comprises a fluid.

10. A method of manufacturing the applicator according to claim 7, said method comprising:
   a. providing the first outer member;
   b. inserting a therapeutic substance into the first outer member such that the therapeutic substance contacts the interior surface of the first outer member between the aperture in the side wall of the first outer member and the first dispensing end of the first outer member;
   c. providing the second inner member;
   d. inserting the second inner member into the first outer member such that the second inner member comes into contact with the therapeutic agent; and
   e. allowing any air or other gas trapped between the proximate end of the second inner member and the therapeutic substance to escape through the aperture in the side wall of the first outer member.

11. The applicator according to claim 6, wherein the proximate end of the second inner member forms a plunger tip, wherein a portion of the plunger tip directly or indirectly contacts the interior surface of the first outer member.

12. The applicator according to claim 11, wherein a portion of the plunger tip directly contacts the interior surface of the first outer member, and the plunger tip and the interior surface of the first outer member form an essentially fluid tight seal.

13. The applicator according to claim 11, wherein a portion of the plunger tip indirectly contacts the interior surface of the first outer member through a sealing member, wherein the sealing member and the interior surface of the first outer member form an essentially fluid tight seal.

14. The applicator according to claim 6, wherein the interior surface of the first outer member has a detent feature and the second inner member has a complementary structure which allows the detent feature to engage and effectively hold the second inner member in place prior to use.

15. The applicator according to claim 14, wherein the detent feature comprises a protrusion on the interior surface of the first outer member and the second inner member comprises a complementary groove which engages the protrusion.

16. The applicator according to claim 15, wherein the aperture located in the side wall of the first outer member is located between the detent feature and the second end of the first outer member.

17. The applicator according to claim 16, wherein the aperture is located in the side wall of the first outer member and is located adjacent to the detent feature such that the aperture is between the detent feature and the second end of the first outer member.

18. The applicator according to claim 6, wherein the second inner member comprises a second chamber, the second chamber being connected by channels located in the second interior member to the chamber defined by a volume created by the interior surface of the first outer member located at or near the dispensing end of the first outer member and the proximate end of the second inner member.

19. The applicator according to claim 6, wherein the chamber further comprises a displacement member.

20. The applicator according to claim 1, wherein the at least one opening is located in the dispensing zone of the first outer member further comprising a seal.

21. The applicator according to claim 20, wherein the seal comprises one of: (a) a ruptureable seal located on an exterior surface of the first outer member such that the ruptureable seal closes the opening, (b) a ruptureable seal located on the interior surface of the first outer member such that the ruptureable seal closes the opening, or (c) a substance contained within the at least one opening,
   wherein the ruptureable seal is ruptureable upon the application of a physical force on the seal, or the substance contained within the opening is removable from the opening upon the application of a force to the substance.

22. The applicator according to claim 20, wherein the dispensing zone of the first outer member comprises a plurality of openings.

23. The applicator according to claim 1, further comprising a retainer located between the second end of the third member and the distal end of the second inner member.

24. The applicator according to claim 1, wherein the therapeutic agent chamber is located in a plunger tip, the plunger tip being located at the proximate end of the second inner member.

25. The applicator according to claim 1, wherein the second inner member comprises a plunger tip located at the proximate end of the second inner member, the plunger tip further comprising a plunger tip chamber and a therapeutic substance within the plunger tip chamber.

26. The applicator according to claim 1, wherein the interior surface of the outer member in the dispensing zone comprises one or more pockets attached thereto, each pocket comprising a therapeutic agent.

27. The applicator according to claim 1, further comprising a shroud attached to the second inner member, said shroud being adapted to contact the body of a user of the applicator.

28. An applicator for introducing a therapeutic substance into a body cavity of a subject, said applicator comprising:
   a. a first outer member having a shape suitable for insertion into a body cavity of a subject, the first outer member comprising at least one side wall, an interior surface, a first dispensing end and a second end distal to the dispensing first end wherein the dispensing end of the first outer member has a dispensing zone comprising at least one opening and the at least one side wall joins the first dispensing end of the first outer member to the second end;
   b. a second inner member having a proximate end and a distal end, the second inner member being coaxially and slidably housed within the first outer member such that the proximate end of the second inner member is within the first outer member, and the distal end of the second inner member extends beyond the second end of the first outer member;

c. a third member extending along a longitudinal axis of the applicator and being housed within the second inner member, the third member comprising a first end which is adjacent a therapeutic agent chamber containing a therapeutic agent, wherein the third member is disposed entirely outside of the therapeutic agent chamber, a second end which extends beyond the distal end of the second inner member, wherein the first end of the third member is adapted to pierce, lance or break the therapeutic agent chamber when the second end of the third member is moved in along the longitudinal axis towards the second inner member, and wherein the therapeutic agent chamber is located in a plunger tip, the plunger tip being located at the proximate end of the second inner member; and d. at least one non-dispensing aperture located in the side wall of the first outer member, wherein the aperture is located at a position on the side wall of the first outer member between the dispensing zone and the second end of the first outer member, further comprising an inner chamber member, the inner chamber member adjacent the dispensing end of the first outer member, the inner chamber member and the plunger tip define an inner chamber, and the inner chamber member and the interior surface of the first outer member define a channel which allows the therapeutic agent to be transported through the openings in the outer member.

29. The applicator according to claim 28, further comprising at least one channel through the plunger tip that allows contents of the inner chamber member to pass from the inner chamber, through the therapeutic agent chamber and to a channel defined by the interior surface of the first outer member and the inner chamber member.

* * * * *